US009855197B2

(12) United States Patent
Itagaki et al.

(10) Patent No.: US 9,855,197 B2
(45) Date of Patent: Jan. 2, 2018

(54) ZINC OXIDE WHICH IS COATED WITH SILICON OXIDE, METHOD FOR MANUFACTURING THE SAME, COMPOSITION WHICH INCLUDES THE ZINC OXIDE COATED WITH SILICON OXIDE, AND COSMETIC

(71) Applicant: Sumitomo Osaka Cement Co., Ltd., Tokyo (JP)

(72) Inventors: Tetsuro Itagaki, Tokyo (JP); Syunsuke Suma, Tokyo (JP); Gaku Fujihashi, Tokyo (JP)

(73) Assignee: SUMITOMO OSAKA CEMENT CO., LTD. (JP)

( * ) Notice: Subject to any disclaimer, the term of this patent is extended or adjusted under 35 U.S.C. 154(b) by 0 days.

(21) Appl. No.: 15/035,620

(22) PCT Filed: Nov. 13, 2014

(86) PCT No.: PCT/JP2014/080039
§ 371 (c)(1),
(2) Date: May 10, 2016

(87) PCT Pub. No.: WO2015/072499
PCT Pub. Date: May 21, 2015

(65) Prior Publication Data
US 2016/0287488 A1 Oct. 6, 2016

(30) Foreign Application Priority Data

Nov. 13, 2013 (JP) ................................. 2013-235347

(51) Int. Cl.
| | | |
|---|---|---|
| *A61K 8/02* | (2006.01) | |
| *A61Q 1/08* | (2006.01) | |
| *A61Q 1/12* | (2006.01) | |
| *A61Q 19/00* | (2006.01) | |
| *A61Q 1/06* | (2006.01) | |
| *A61K 8/25* | (2006.01) | |
| *C09C 1/04* | (2006.01) | |
| *A61K 8/27* | (2006.01) | |
| *A61Q 17/04* | (2006.01) | |
| *A61Q 1/10* | (2006.01) | |

(52) U.S. Cl.
CPC .............. *A61K 8/0241* (2013.01); *A61K 8/25* (2013.01); *A61K 8/27* (2013.01); *A61Q 1/06* (2013.01); *A61Q 1/08* (2013.01); *A61Q 1/10* (2013.01); *A61Q 1/12* (2013.01); *A61Q 17/04* (2013.01); *A61Q 19/007* (2013.01); *C09C 1/043* (2013.01); *A61K 2800/412* (2013.01); *A61K 2800/413* (2013.01); *A61K 2800/621* (2013.01); *C01P 2002/76* (2013.01); *C01P 2002/77* (2013.01); *C01P 2004/62* (2013.01); *C01P 2004/64* (2013.01); *C01P 2004/84* (2013.01)

(58) Field of Classification Search
None
See application file for complete search history.

(56) References Cited

U.S. PATENT DOCUMENTS

| | | | | | |
|---|---|---|---|---|---|
| 4,375,373 | A | * | 3/1983 | Abe ........................ | C09C 3/063 106/403 |
| 5,230,833 | A | * | 7/1993 | Romberger .......... | C01B 33/1435 252/363.5 |
| 6,660,380 | B1 | * | 12/2003 | Ishida ...................... | A61K 8/11 427/215 |
| 2008/0070140 | A1 | * | 3/2008 | Fomitchev .............. | C09C 3/041 430/108.3 |
| 2010/0003202 | A1 | * | 1/2010 | Matsumoto ............ | A61K 8/027 424/59 |
| 2010/0008872 | A1 | * | 1/2010 | Katusic .................... | A61K 8/25 424/59 |

FOREIGN PATENT DOCUMENTS

| | | |
|---|---|---|
| EP | 0988853 A1 | 3/2000 |
| EP | 1317245 A2 | 6/2003 |
| JP | H03-153766 A | 7/1991 |
| JP | H03153766 * | 7/1991 |
| JP | 2851885 B2 | 1/1999 |
| JP | H11-302015 A | 11/1999 |
| JP | 2003-112923 A | 4/2003 |
| JP | 2003112923 * | 4/2003 |
| JP | 2004-059421 A | 2/2004 |
| JP | 3520785 B2 | 4/2004 |
| JP | B-3570730 | 9/2004 |
| JP | 3848458 B2 | 11/2006 |
| JP | 2009-545509 A | 12/2009 |
| JP | 4836232 B2 | 12/2011 |
| JP | A-2013-142103 | 7/2013 |
| WO | 02/22098 A2 | 3/2002 |
| WO | WO2008019905 A1 | 6/2007 |

OTHER PUBLICATIONS

International Search Report of PCT/JP2014/080039 dated Feb. 17, 2015.
Third Party Submission filed for PCT/JP2014/080039, Mar. 8, 2016 (6 pages).
Grasset et al., "Surface modification of zinc oxide nanoparticles by aminopropyltriethoxysilane," Journal of Alloys and Compounds, 360(1-2):298-311 (2003).
Search Report for European Patent Application No. 14862379.6 (dated Apr. 4, 2017).

* cited by examiner

*Primary Examiner* — Robert A Wax
*Assistant Examiner* — Caralynne Helm
(74) *Attorney, Agent, or Firm* — Merchant & Gould P.C.

(57) ABSTRACT

Zinc oxide coated with silicon oxide of the present invention is zinc oxide which is coated with silicon oxide wherein surfaces of zinc oxide particles are coated with silicon oxide coatings, and the coated zinc oxide particles comprises at least one element selected from a group consisting of Mg, Ca, and Ba.

8 Claims, 1 Drawing Sheet

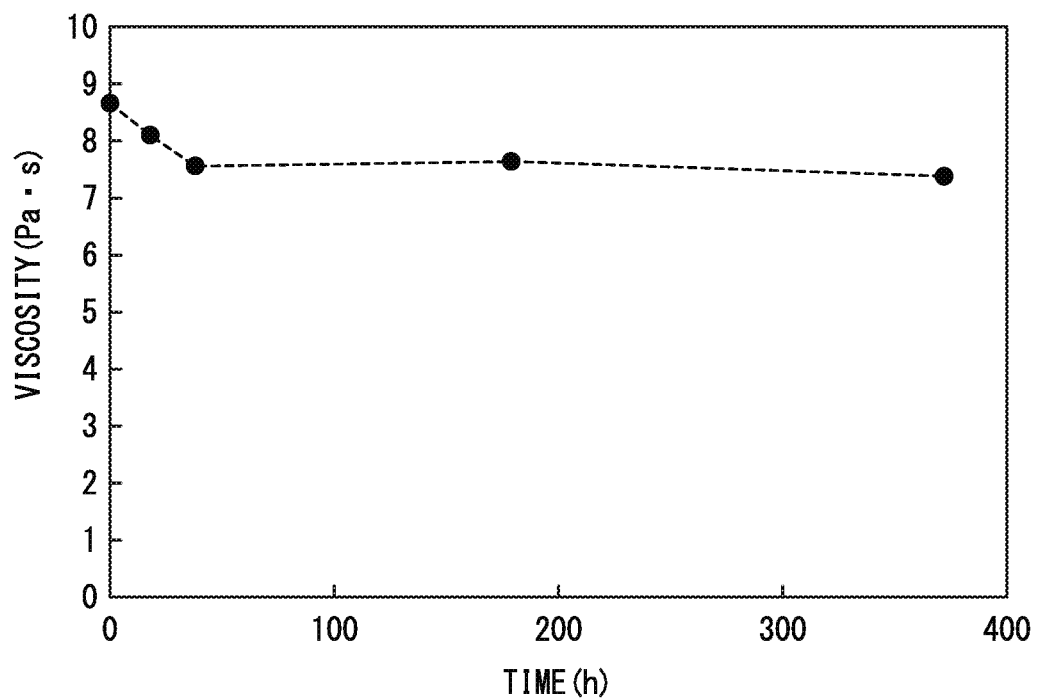

ically activity of zinc oxide, there is proposed surface-coated zinc oxide in which the surface of zinc oxide is coated with a low-active substance such as silicon oxide or aluminum oxide (for example, refer to Patent Literature 1 and 2).

ZINC OXIDE WHICH IS COATED WITH SILICON OXIDE, METHOD FOR MANUFACTURING THE SAME, COMPOSITION WHICH INCLUDES THE ZINC OXIDE COATED WITH SILICON OXIDE, AND COSMETIC

TECHNICAL FIELD

The present invention relates to zinc oxide which is coated with silicon oxide and a method for manufacturing the same, a composition which includes zinc oxide coated with silicon oxide, and a cosmetic.

This present application is a U.S. National Stage Application under 35 U.S.C. §371 of International Application No. PCT/JP2014/080039 filed Nov. 13, 2014, which claims the benefit of priority to Japanese Patent Application No. 2013-235347, filed on Nov. 13, 2013, the contents of all of which are hereby incorporated by reference in their entireties.

BACKGROUND ART

It is said that ultraviolet rays may become causes of not only suntan or sunburn but also aging phenomena or skin cancer. Therefore, ultraviolet-shielding agents are widely used in the cosmetics field.

For example, as ultraviolet-shielding agents, organic ultraviolet absorbers such as benzophenone-based absorbers, methoxycinnamic acid-based absorbers, and dibenzoyl methane-based absorbers or inorganic ultraviolet-scattering agents such as zinc oxide and titanium oxide are generally used.

However, for organic ultraviolet absorbers, there are problems of a concern that organic ultraviolet absorbers may deteriorate due to heat or irradiation with ultraviolet rays for a long period of time and a necessity of the combined use of multiple kinds of organic ultraviolet absorber having different ultraviolet-absorbing wavelengths since it is not possible to absorb a wide range of ultraviolet rays with only one kind of organic ultraviolet absorber.

On the other hand, inorganic ultraviolet-scattering agents have advantages that inorganic ultraviolet-scattering agents do not deteriorate due to heat or irradiation with ultraviolet rays for a long period of time, are excellent in terms of weather resistance, heat resistance, and the like, and are capable of scattering ultraviolet rays in a wide wavelength range. However, for inorganic ultraviolet-scattering agents having the above-described advantages as well, there are problems as described below. That is, inorganic ultraviolet-scattering agents scatter not only ultraviolet rays but also visible light rays, and thus, when a large amount of the inorganic ultraviolet-scattering agents are formulated into cosmetics or the like, there is a problem in that the face is likely to be white. Therefore, in order to cope with the above-described problem, the inorganic ultraviolet-scattering agents are used in a form of being appropriately combined with organic ultraviolet absorbers.

Recently, water-based cosmetics have been being used particularly as a variety of cosmetics such as sunscreens, emulsions, and creams since water-based cosmetics are not sticky and provide a silky feeling compared with oil-based cosmetics. In the above-described cosmetics, titanium oxide and zinc oxide are mainly used as inorganic ultraviolet-scattering agents.

Meanwhile, zinc oxide has photocatalytic activity. Therefore, when zinc oxide is used in cosmetics, troublesomely, it is necessary to strictly select the amount of zinc oxide formulated or other components formulated with zinc oxide. Therefore, for the purpose of suppressing the photocatalytic activity of zinc oxide, there is proposed surface-coated zinc oxide in which the surface of zinc oxide is coated with a low-active substance such as silicon oxide or aluminum oxide (for example, refer to Patent Literature 1 and 2).

Meanwhile, in a case in which zinc oxide is used in water-based cosmetics, intrinsic problems of water-based cosmetics are caused. That is, since zinc oxide is an oxide of an ampholytic metal, zinc oxide readily dissolves in acids and alkalis and also dissolves slightly in water and, consequently, discharges zinc ions. Therefore, in a case in which zinc oxide is used in water-based cosmetics, there has been a concern that eluting zinc ions may react with water-soluble polymers and the like of organic ultraviolet absorbers and viscosity improvers and problems of the degradation of cosmetic performance, changes in color and viscosity, and the like may be caused. That is, there has been a problem in that the degree of freedom in terms of formulation is restricted.

Particularly, when carbomers such as carboxy vinyl polymers which are ordinarily used as viscosity improvers and zinc oxide are jointly used, there is a problem in that eluting zinc ions and carboxylate groups (COO—) react with each other, and thus the gel structures of the carbomers are broken, and the viscosity decreases. Therefore, in order to suppress the elution of zinc ions, there is proposed surface-coated zinc oxide in which the surface is coated with an inorganic compound such as silicon oxide (for example, refer to Patent Literature 3 and 4).

CITATION LIST

Patent Literature

[Patent Literature No. 1] Japanese Patent No. 2851885
[Patent Literature No. 2] Japanese Patent No. 3848458
[Patent Literature No. 3] Japanese Patent No. 3520785
[Patent Literature No. 4] Japanese Patent No. 4836232

SUMMARY OF INVENTION

Technical Problem

However, in a case in which surface-coated zinc oxide as described in Patent Literature 1 to 4 is used in water-based cosmetics, there has been a problem in that the hydrogen-ion exponents (pH) of the water-based cosmetics change to be alkaline (7<) and quality stability also deteriorates.

Particularly, in recent cosmetics, there is a tendency of the content of water being increased in order to provide a feeling that is more similar to water. In a case in which the content of water is increased, the problem of the quality degradation due to an increase in the hydrogen-ion exponent becomes more significant.

The present invention has been made in consideration of the above-described circumstances, and an object of the present invention is to provide zinc oxide coated with silicon oxide, which can suppress variation in the hydrogen-ion exponent (pH), a method for manufacturing the same, and a composition and a cosmetic which include the zinc oxide coated with silicon oxide.

Solution to Problem

As a result of repetitive intensive studies for solving the above-described problems, the present inventors and the like found the following inventions. That is, it was found that, when zinc oxide which is coated with silicon oxide wherein the surfaces of zinc oxide particles are coated with silicon oxide coatings contains, and the coated zinc oxide particles comprises at least one element selected from a group consisting of Mg, Ca, and Ba, even in a case in which this zinc oxide which is coated with silicon oxide is applied to water-based materials such as water-based cosmetics, the hydrogen-ion exponents (pH) of the water-based materials do not change and quality stability can be maintained, and the present inventors and the like completed the present invention.

That is,

[1] According to a first aspect of the present invention, there is provided Zinc oxide which is coated with silicon oxide, wherein the surfaces of zinc oxide particles are coated with silicon oxide coatings, and the coated zinc oxide particles comprises at least one element selected from a group consisting of Mg, Ca, and Ba.

[2] According to a second aspect of the present invention, there is provided a method of manufacturing zinc oxide which is coated with silicon-oxide, comprising: mixing, in a solution including water, at least one element selected from a group consisting of Mg, Ca, and Ba and zinc oxide wherein surfaces of zinc oxide particles are coated with silicon oxide containing an alkali metal to replace the alkali metal, which is included in the zinc oxide coated with silicon oxide, to the at least one element selected from a group consisting of Mg, Ca, and Ba.

[3] According to a third aspect of the present invention, there is provided a method of manufacturing zinc oxide which is coated with silicon-oxide, comprising:

preparing a water-based suspension which includes zinc oxide particles and alkali metal silicate by adding a zinc oxide water-based suspension which includes zinc oxide particles to an alkali metal silicate aqueous solution which includes alkali metal silicate;

adding an acid to the water-based suspension; and adding an aqueous solution which includes at least one selected from a group consisting of magnesium salts, calcium salts and barium salts to the water-based suspension to which the acid has been added to perform ion-exchange wherein alkali metal ions derived from the alkali metal silicate is exchanged with ions of at least one selected from a group consisting of Mg, Ca, and Ba.

[4] According to a fourth aspect of the present invention, there is provided a composition which includes zinc oxide coated with silicon oxide of the present invention.

[5] According to a fifth aspect of the present invention, there is provided a cosmetic containing the zinc oxide which is coated with silicon oxide of the present invention in a base material thereof.

Effects of Invention

According to the zinc oxide which is coated with silicon oxide of the present invention, since at least one element selected from a group consisting of Mg, Ca, and Ba is contained in the zinc oxide, even in a case in which the zinc oxide which is coated with silicon oxide is applied to water-based materials such as water-based cosmetics, it is possible to suppress a change in the hydrogen-ion exponents (pH) of the water-based materials. Therefore, it is possible to maintain the stability of the qualities of the water-based materials.

According to the method for manufacturing zinc oxide which is coated with silicon oxide of the present invention, the method includes a step wherein, in a solution including water, at least one element selected from a group consisting of Mg, Ca, and Ba and is mixed with zinc oxide wherein surfaces of zinc oxide particles are coated with silicon oxide and contains an alkali metal, in order to replace the alkali metal, which is included in the zinc oxide coated with silicon oxide, to the at least one element selected from a group consisting of Mg, Ca, and Ba. As a result, it is possible to add at least one element selected from a group consisting of Mg, Ca, and Ba to zinc oxide which is coated with silicon oxide. Therefore, even in a case in which the zinc oxide which is coated with silicon oxide is applied to water-based materials such as water-based cosmetics, it is possible to suppress a change in the hydrogen-ion exponents (pH) of the water-based materials, and thus it is possible to produce zinc oxide which is coated with silicon oxide capable of maintaining the stability of the qualities of the water-based materials.

According to the method for manufacturing zinc oxide which is coated with silicon oxide of the present invention, the method includes steps of: preparing a water-based suspension which includes zinc oxide particles and alkali metal silicate by adding a zinc oxide water-based suspension which includes zinc oxide particles to an alkali metal silicate aqueous solution which includes alkali metal silicate; adding an acid to the water-based suspension; and adding an aqueous solution which includes at least one selected from a group consisting of magnesium salts, calcium salts and barium salts to the water-based suspension to which the acid has been added to perform ion-exchange wherein alkali metal ions derived from the alkali metal silicate is exchanged with ions of at least one selected from a group consisting of Mg, Ca, and Ba. As a result, it is possible to add at least one element selected from a group consisting of Mg, Ca, and Ba to zinc oxide which is coated with silicon oxide. Therefore, even in a case in which the zinc oxide which is coated with silicon oxide is applied to water-based materials such as water-based cosmetics, it is possible to suppress a change in the hydrogen-ion exponents (pH) of the water-based materials, and thus it is possible to produce zinc oxide which is coated with silicon oxide capable of maintaining the stability of the qualities of the water-based materials.

According to the composition which includes zinc oxide coated with silicon oxide of the present invention, since the zinc oxide which is coated with silicon oxide of the present invention is contained, not only in a case in which the composition is applied to oil-based materials such as water-in-oil (W/O) materials but also in a case in which the composition is applied to water-based materials, it is possible to suppress a change in the hydrogen-ion exponents (pH) of the water-based materials. Therefore, it is possible to maintain the stability of qualities.

According to the cosmetic of the present invention, the cosmetic comprises the zinc oxide coated with silicon oxide of the present invention in a base material thereof. Accordingly, it is possible to suppress variation in the hydrogen-ion exponents (pH) of the cosmetic, not only in a case in which the cosmetic is used as oil-based cosmetics such as water-in-oil (W/O) type cosmetic, but also in a case in which the cosmetic is used as water-based cosmetics. Therefore, it is possible to maintain the stability of qualities.

BRIEF DESCRIPTION OF DRAWINGS

FIG. 1 is a view illustrating a temporal change in the viscosity of a composition which includes zinc oxide coated with silicon oxide of Example 3 of the present invention.

DESCRIPTION OF EMBODIMENTS

The present invention relates to zinc oxide which is coated with silicon oxide and a method for manufacturing the same, a composition which includes zinc oxide coated with silicon oxide, and a cosmetic. In more detail, the present invention relates to zinc oxide which is coated with silicon oxide that is preferably used in a variety of cosmetic products such as skin care cosmetic products, makeup cosmetic products, and body care cosmetic products, particularly, skin lotions, sunscreen gels, emulsions, creams, foundations, lipsticks, blushers, eye shadows, and the like which require an ultraviolet-shielding function and a method for manufacturing the same, a composition which includes zinc oxide coated with silicon oxide, and a cosmetic including the zinc oxide which is coated with silicon oxide in a base material.

Hereinafter, preferred embodiments of the zinc oxide which is coated with silicon oxide and the method for manufacturing the same, the composition which includes zinc oxide coated with silicon oxide, and the cosmetic of the present invention will be described.

Meanwhile, the following embodiments are specific descriptions for the easier understanding of the purport of the invention and do not limit the present invention unless particularly designated.

[Zinc Oxide which is Coated with Silicon Oxide]

Zinc oxide which is coated with silicon oxide of a first embodiment of the present invention is zinc oxide which is coated with silicon oxide, wherein the surfaces of zinc oxide particles are coated with silicon oxide coatings, and the coated zinc oxide particles comprises at least one element selected from a group consisting of Mg, Ca, and Ba.

The average particle diameter of the zinc oxide which is coated with silicon oxide of the present embodiment can be selected as necessary and is preferably 2 nm or more and 500 nm or less, more preferably 5 nm or more and 400 nm or less, and still more preferably 10 nm or more and 400 nm or less.

Meanwhile, the "average particle diameter" in the present embodiment refers to a value obtained using the following method. That is, the zinc oxide which is coated with silicon oxide of the present embodiment is observed using a transmission electron microscope (TEM) or the like, and a predetermined number, for example, 200 particles, or 100 particles, of zinc oxide particles coated with silicon oxide are selected. Then, the longest linear portions (the largest long diameters) of the selected zinc oxide particles which have been coated with silicon oxide are measured, and the weighted average of the measured values is obtained.

In a case in which aggregate of zinc oxide particles coated with silicon oxide is generated, what needs to be measured is not the diameter of the aggregate. Instead, the predetermined number of particles (primary particles) of zinc oxide coated with silicon oxide, which are included in the aggregate, are observed, and the average particle diameter of the particles is obtained.

The reasons for limiting the average particle diameter of the particles of the zinc oxide which is coated with silicon oxide of the present embodiment in the above-described range are as described below. When the average particle diameter is less than 2 nm, the crystal structure of zinc oxide is a space group No. 186, $P6_3mc$, $a=0.32498$ nm, and $c=0.52066$ nm, and thus sufficient crystallinity cannot be obtained, and the ultraviolet-shielding performance of zinc oxide degrades, which is not preferable. On the other hand, when the average particle diameter exceeds 500 nm, the visible light-scattering intensities of the particles are dependent on the particle diameters, and thus there is a concern that, in a case in which the zinc oxide which is coated with silicon oxide is formulated into cosmetics or the like, it may become difficult to maintain transparency.

Meanwhile, as the average particle diameter of the zinc oxide which is coated with silicon oxide of the present embodiment decreases, the zinc oxide which is coated with silicon oxide becomes more suitable for enhancing transparency during use in a case in which the zinc oxide which is coated with silicon oxide is formulated into cosmetics. On the other hand, as the average particle diameter of the zinc oxide which is coated with silicon oxide of the present embodiment increases, the ultraviolet ray-scattering intensities also increase, and it is possible to shield ultraviolet rays having long wavelengths. Therefore, the average particle diameter of the zinc oxide which is coated with silicon oxide of the present embodiment may be appropriately selected in accordance with the transparency and ultraviolet-shielding properties of intended cosmetics.

The content rate of zinc oxide particles in the zinc oxide which is coated with silicon oxide of the present embodiment can be selected as necessary and is preferably 50% by mass or more and 99% by mass or less, more preferably 70% by mass or more and 95% by mass or less, and still more preferably 70% by mass or more and 90% by mass or less.

Here, when the content rate of zinc oxide particles in the zinc oxide which is coated with silicon oxide is less than 50% by mass, there is a possibility that a desired ultraviolet-shielding effect cannot be obtained. In cosmetics including the above-described zinc oxide which is coated with silicon oxide in a base material thereof, in order to obtain a desired ultraviolet-shielding effect, it is necessary to use a large amount of the zinc oxide which is coated with silicon oxide, which is not preferable. On the other hand, when the content rate of zinc oxide particles in the zinc oxide which is coated with silicon oxide exceeds 99% by mass, there is a possibility that the proportion of zinc oxide particles in the zinc oxide which is coated with silicon oxide may excessively increase. As a result, it becomes impossible to sufficiently coat the surfaces of zinc oxide particles with silicon oxide coatings, and there is a possibility that the photocatalytic activity of zinc oxide or the suppression of zinc ion elution may become insufficient. As a result, there is a concern that the formulation stability may be impaired in a case in which the zinc oxide which is coated with silicon oxide is jointly used with organic effective components such as natural oils and organic ultraviolet absorbers in cosmetics, which is not preferable.

The content rate of silicon oxide in the zinc oxide which is coated with silicon oxide of the present embodiment may be appropriately adjusted depending on the average particle diameter of zinc oxide. For example, for zinc oxide having an average particle diameter of 50 nm or less, the content rate of silicon oxide is preferably 3% by mass or more and 45% by mass or less. For zinc oxide having an average particle diameter of more than 50 nm, the content rate of silicon oxide is preferably 1% by mass or more and 35% by mass or less.

The zinc oxide which is coated with silicon oxide of the present embodiment contains at least one element selected from a group consisting of Mg, Ca, and Ba.

It is preferable that the silicon oxide coatings include said at least one element selected from a group consisting of Mg, Ca and Ba, and a total mass percentage of said element included in the silicon oxide coating is greater than a mass percentage of an alkali metal included in the silicon oxide coatings. Furthermore, the ratio of the mass percentage of the alkali metal in the silicon oxide coatings to the total mass percentage of at least one element selected from a group consisting of Mg, Ca, and Ba in the silicon oxide coatings (the mass percentage of the alkali metal/the mass percentage of Mg, Ca, and Ba) is preferably 0.001 or more and 0.6 or less, more preferably 0.01 or more and 0.5 or less, and still more preferably 0.1 or more and 0.4 or less.

In the present invention, the alkali metal refers to an ordinarily-known alkali metal and, specifically, refers to at least one alkali metal selected from a group consisting of lithium, sodium, potassium, rubidium, cesium, and francium.

Here, the reason for setting the total mass percentage of at least one element selected from a group consisting of Mg, Ca, and Ba in the silicon oxide coatings to be greater than the mass percentage of the alkali metal in the silicon oxide coatings is that the main cause for a change in the hydrogen-ion exponent (pH) of the zinc oxide which is coated with silicon oxide of the present embodiment in the initial phase is not the elution of zinc ions but the elution of alkali metal ions in the silicon oxide coatings.

Meanwhile, in a case in which at least one element selected from a group consisting of Mg, Ca, and Ba is included in the silicon oxide coatings in the zinc oxide which is coated with silicon oxide, the element is present in a form of magnesium silicate, calcium silicate, barium silicate, or the like which has a low solubility in water. Therefore, at least one element selected from a group consisting of Mg, Ca, and Ba barely elutes even when included in the silicon oxide coatings in the zinc oxide which is coated with silicon oxide. Therefore, when the total mass percentage of at least one element selected from a group consisting of Mg, Ca, and Ba in the silicon oxide coatings is set to be far greater than the mass percentage of the alkali metal in the silicon oxide coatings in the zinc oxide which is coated with silicon oxide of the present embodiment by substituting alkali metal ions in the zinc oxide which is coated with silicon oxide with at least one element selected from a group consisting of Mg, Ca, and Ba, the following effect can be obtained. That is, the elution of alkali metal ions in the zinc oxide which is coated with silicon oxide can be further suppressed. In addition, as a result, it is possible to suppress a change in the hydrogen-oxygen exponent (pH) of the zinc oxide which is coated with silicon oxide.

That is, when alkali metal ions in the zinc oxide which is coated with silicon oxide are substituted with at least one element selected from a group consisting of Mg, Ca, and Ba, the alkali metal in the silicon oxide coatings in the zinc oxide which is coated with silicon oxide is removed from the silicon oxide coatings in the zinc oxide which is coated with silicon oxide. Meanwhile, at least one element selected from a group consisting of Mg, Ca, and Ba substituting the alkali metal in the silicon oxide coatings is present in the silicon oxide coatings in the zinc oxide which is coated with silicon oxide after the substitution. These Mg, Ca, and Ba used for substitution are present in a form of magnesium silicate, calcium silicate, barium silicate, or the like which has a low solubility in water. As a result of the above-described step, the total mass percentage of at least one element selected from a group consisting of Mg, Ca, and Ba in the silicon oxide coatings in the zinc oxide which is coated with silicon oxide of the present embodiment becomes greater than the mass percentage of the alkali metal in the silicon oxide coatings, even when the zinc oxide is mixed with water-based materials, the elution of the alkali metal is suppressed, and a change in the hydrogen-ion exponent (pH) can be suppressed.

The sum total of the mass percentages of the alkali metals in the silicon oxide coatings in the zinc oxide which is coated with silicon oxide of the present embodiment is preferably 0.8% by mass or less, more preferably 0.6% by mass or less, and still more preferably 0.2% by mass or less. The lower limit value of the mass percentage of the alkali metal in the silicon oxide coatings can be arbitrarily selected. The mass percentage of the alkali metal may be 0% and, as another example, may be, for example, 0.0001% by mass or more, 0.001% by mass or more, or the like.

The total mass percentage of at least one element selected from a group consisting of Mg, Ca, and Ba in the silicon oxide coatings in the zinc oxide which is coated with silicon oxide of the present embodiment is preferably 0.01% by mass or more and 1% by mass or less.

The mass percentage (% by mass) of the alkali metal, Mg, Ca, and Ba which are included in the zinc oxide which is coated with silicon oxide (or included in the silicon oxide coatings thereof) of the present embodiment can be measured by the atomic absorption analysis method.

In the zinc oxide which is coated with silicon oxide of the present embodiment, a decomposition rate of Brilliant Blue which is caused by a photocatalytic activity of particles of the coated zinc oxide is preferably 3% or less, more preferably 2% or less, and still more preferably 1% or less. The measurement of Brilliant Blue will be explained below.

Hereinafter, the reason why 3% or less of the decomposition rate of Brilliant Blue that is caused by the photocatalytic activity of particles of the coated zinc oxide is preferable will be described. The reason is that, 3% or less of the decomposition rate of Brilliant Blue means that the photocatalytic activity of the zinc oxide particles has been suppressed, and thus excellent homogeneity of the silicon oxide coatings which coat zinc oxide particles has been achieved. Here, the excellent homogeneity of the silicon oxide coatings which coat zinc oxide particles means that there is no coating unevenness, the coatings are not localized, and there are not pin holes and the like. The decomposition rate of Brilliant Blue is used as an index of the photocatalytic activity of the zinc oxide particles. A photocatalytic reaction of the zinc oxide particles basically occurs on the surfaces of the zinc oxide particles. That is, it means that, the lower the low decomposition rate of Brilliant Blue that is caused by the photocatalytic activity of zinc oxide particles is, the smaller an exposed area, from which silicon oxide is exposed on the surface of the zinc oxide coated with silicon oxide, is.

Meanwhile, in a case in which the decomposition rate of Brilliant Blue exceeds 3%, the photocatalytic activity of zinc oxide particles is not suppressed, and thus the surfaces of the zinc oxide particles are partially covered with the silicon oxide coatings. That is, it means that the homogeneity of the silicon oxide coatings is poor.

A method for measuring the decomposition rate of Brilliant Blue is as described below.

First, an aqueous solution of Brilliant Blue having a content rate of Brilliant Blue adjusted to be a predetermined value (for example, 5 ppm) is prepared. Next, a predetermined amount of the aqueous solution of Brilliant Blue is sampled from the aqueous solution of Brilliant Blue using a screw tube. Next, 1% by mass (in terms of zinc oxide) of zinc oxide which is coated with silicon oxide of the mass of the liquid was injected into the sampled aqueous solution of Brilliant Blue and is ultrasonic-dispersed, thereby preparing a suspension. Next, this suspension is irradiated with ultraviolet rays having predetermined wavelengths from a predetermined distance (for example, 10 cm) for a predetermined period of time (for example, six hours).

As an ultraviolet radiation lamp, for example, a sterilized lamp GL20 (wavelength: 253.7 nm, ultraviolet ray output: 7.5 W, manufactured by Toshiba Corporation) can be used.

Next, a supernatant liquid is sampled from the suspension irradiated with the ultraviolet rays. The absorptiometric spectra of the aqueous solution of Brilliant Blue and the supernatant liquid are respectively measured by means of atomic absorption spectrometry. The decomposition rate D of Brilliant Blue is calculated from Equation (1) below using the measurement values.

$$D=(A_0-A_1)/A_0 \quad (1)$$

Here, in Equation (1) above, $A_0$ denotes the absorbance at the absorption maximum wavelength (630 nm) of the absorptiometric spectrum of the aqueous solution of Brilliant Blue (5 ppm), and $A_1$ denotes the absorbance at the absorption maximum wavelength of the absorptiometric spectrum of the supernatant liquid.

Meanwhile, for ordinary zinc oxide (the average particle diameter of 35 nm; manufactured by Sumitomo Osaka Cement Co., Ltd.), the decomposition rate of Brilliant Blue was measured on the basis of the above-described method and, consequently, was found to be 90%. From this result, it was confirmed that, when this zinc oxide (the average particle diameter of 35 nm; manufactured by Sumitomo Osaka Cement Co., Ltd.) has a photocatalytic activity, the decomposition rate of Brilliant Blue is high.

In the zinc oxide which is coated with silicon oxide of the present embodiment, it is preferable that, when an abundance ratio of silicon included in the silicon oxide coatings in a $Q^3$ environment is denoted by $Q^3$, and the abundance ratio of silicon included in the silicon oxide coatings in a $Q^4$ environment is denoted by $Q^4$, the abundance ratios satisfy $Q^3+Q^4 \geq 0.6$ and $Q^4/(Q^3+Q^4) \geq 0.5$. Preferred reasons and $Q^n$ will be described below.

The condensation degree, that is, the degree of condensation of silicon oxide in the zinc oxide which is coated with silicon oxide of the present embodiment can be found using the following method. That is, for the zinc oxide which is coated with silicon oxide, an NMR spectrum is measured by means of MAS-nuclear magnetic resonance (NMR) spectroscopy in which solid $^{29}Si$ is used. In addition, the area ratios of signals belonging to individual environments $Q^0$, $Q^1$, $Q^2$, $Q^3$, and $Q^4$ are measured from the peak area ratio of this NMR spectrum, whereby the condensation degree can be easily found.

Here, $Q^n$ (n=0 to 4) denotes a chemical structure determined depending on the number of crosslinking oxygen atoms, that is, oxygen atoms that bond to two Si atoms among oxygen atoms in a $SiO_2$ tetrahedral unit which is a constituent unit of silicon oxide.

The area ratios of signals belonging to the respective environments $Q^0$, $Q^1$, $Q^2$, $Q^3$, and $Q^4$ are denoted by $Q^0$, $Q^1$, $Q^2$, $Q^3$, and $Q^4$. Here, $Q^0+Q^1+Q^2+Q^3+Q^4=1$.

When the abundance ratio of silicon in the silicon oxide coatings of the zinc oxide coated with silicon oxide of the present embodiment in the $Q^3$ environment is denoted by $Q^3$, and the abundance ratio of silicon in the silicon oxide coatings in the $Q^4$ environment is denoted by $Q^4$, the abundance ratios preferably satisfy $Q^3+Q^4 \geq 0.6$ and $Q^4/(Q^3+Q^4) \geq 0.5$.

Here, in a case in which $Q^3+Q^4 \geq 0.6$ is satisfied, but $Q^4/(Q^3+Q^4) \geq 0.5$ is less than 0.5 ($Q^4/(Q^3+Q^4)<0.5$), silicon oxide in the silicon oxide coatings does not sufficiently condense, and there is a concern that the zinc ion elution suppression effect of the zinc oxide which is coated with silicon oxide cannot be sufficiently obtained, which is not preferable.

[Method for Manufacturing Zinc Oxide which is Coated with Silicon Oxide]

(1) First Embodiment

A method of manufacturing the zinc oxide coated by silicon oxide of the present embodiment is the method shown below. That is, a manufacturing method is provided which includes a step (hereinafter, it may be referred to as the "substitution step") wherein, in a solution including water, at least one element selected from a group consisting of Mg, Ca, and Ba and zinc oxide wherein surfaces of zinc oxide particles are coated with silicon oxide containing an alkali metal are mixed to replace the alkali metal, which coats the silicon oxide, to the at least one element selected from a group consisting of Mg, Ca, and Ba.

Next, the method of manufacturing zinc oxide which is coated with silicon oxide of the present embodiment will be described in detail.

As the zinc oxide coated with silicon oxide containing an alkali metal, zinc oxide in which surfaces of zinc oxide particles are coated with silicon oxide by reacting silicate containing an alkali metal such as silicate soda and zinc oxide particles may be used. Alternatively, zinc oxide coated with commercially available silicon oxide may be used.

As a method of coating the surfaces of zinc oxide particles with silicon oxide, it is possible to use, for example, methods described in Japanese Laid-open Patent Publication No. H03-183620, Japanese Laid-open Patent Publication No. H11-256133, Japanese Laid-open Patent Publication No. H11-302015, and Japanese Laid-open Patent Publication No. 2007-016111.

Meanwhile, when or after silicate and zinc oxide are reacted together, sodium aluminate, aluminum nitrate, aluminum sulfate, titanyl sulfate, or the like may be added thereto, so that aluminum oxide, titanium oxide, or the like can be included in the silicon oxide coatings, or an aluminum oxide coating or a titanium oxide coating can be formed on the surface of the silicon oxide coating.

A method of coating the surfaces of zinc oxide particles with silicon oxide and aluminum oxide can be selected as necessary, and examples thereof include the following method. First, zinc oxide particles and water are mixed together and then are ultrasonic-dispersed, thereby preparing a zinc oxide water-based suspension.

Next, this suspension is heated, an aqueous solution of sodium silicate is added thereto while stirring the suspension, and the suspension is aged for 10 minutes to 60 minutes.

Next, an acid such as a diluted acid is added to the suspension under stirring so as to adjust the pH to be 5 to 9, and the suspension is aged for 30 minutes to five hours.

Next, an aqueous solution of sodium aluminate is added to the suspension under stirring, and the suspension is aged for 10 minutes to 60 minutes.

Next, a diluted acid is added to the suspension under stirring so as to adjust the pH to be 5 to 9, and the suspension is aged for 30 minutes to five hours.

Next, this reaction liquid is separated into solid and liquid, the obtained reactant is cleaned using a solvent such as water and, furthermore, is dried at approximately 100° C. to 200°

C., thereby obtaining zinc oxide particles which are coated with silicon oxide wherein an alkali metal is included.

[Substitution Step]

The substitution step is required to be carried out, after the step is completed wherein the surfaces of zinc oxide particles are coated with silicon oxide which contains an alkali metal. A reason therefor is that, when silicate including an alkali metal and at least one element selected from a group consisting of Mg, Ca, and Ba are mixed together in a solution which simply includes water, at least one precipitate of magnesium silicate, calcium silicate and barium silicate is generated as impurities. Therefore, the substitution step is preferably provided in any stage between a point in time after the step is performed wherein zinc oxide is coated with silicon oxide by a neutralization reaction or the like of silicate and a point in time after the drying step is performed. According to the above-described method, processes used for a reaction can be reduced, and it is possible to obtain the zinc oxide which is coated with silicon oxide of the present embodiment at a low cost.

First, zinc oxide coated with silicon oxide which contains an alkali metal and at least one element selected from a group consisting of Mg, Ca, and Ba are added to a solution including watern and mixing thereof is performed.

The solution including water is not particularly limited and can be selected as necessary. For example, water or a solution obtained by mixing water and a solvent compatible with water can be used.

Preferred examples of the solvent compatible with water include protic polar solvents such as methanol, ethanol, and 2-propanol and aprotic polar solvents such as acetone and tetrahydrofuran. Among these, protic polar solvents such as methanol, ethanol, and 2-propanol are more preferred.

The reaction temperature in this mixing treatment is not particularly limited and can be selected as necessary. The reaction temperature may be equal to or higher than the solidification point of a solvent in a mixed liquid including the zinc oxide coated with silicon oxide, at least one element selected from a group consisting of Mg, Ca, and Ba, and the solution including water.

In addition, although the reaction proceeds even when the mixed liquid is left to stand, in order to increase the reaction efficiency, it is preferable to react the mixed liquid under stirring.

The reaction duration is not particularly limited and can be selected as necessary. A reaction duration of one hour or longer is preferred.

By means of this mixing treatment, the alkali metal in the zinc oxide coated with silicon oxide is substituted with at least one element selected from a group consisting of Mg, Ca, and Ba and elutes into the mixed liquid from the zinc oxide coated with silicon oxide. Meanwhile, the ions of at least one element selected from a group consisting of Mg, Ca, and Ba which substitutes the alkali metal are injected into the zinc oxide which is coated with silicon oxide by substituting the alkali metal, and consequently, zinc oxide which is coated with silicon oxide including at least one element selected from a group consisting of Mg, Ca, and Ba is obtained.

The amount of at least one element selected from a group consisting of Mg, Ca, and Ba which are included in the mixed liquid is not particularly limited and can be selected as necessary. In order to perform ion-exchange wherein alkali ions such as Na and K included in the zinc oxide coated with silicon oxide is exchanged for ions of at least one element selected from a group consisting of Mg, Ca, and Ba, the amount of the element is preferably equal to or more than the sum of the molar equivalents of the alkali metal included in the zinc oxide coated with silicon oxide.

A raw material for providing at least one element selected from a group consisting of Mg, Ca, and Ba may be an inorganic salt including the above-described elements and is not particularly limited. For example, magnesium chloride, calcium chloride, barium chloride, magnesium sulfate, magnesium nitrate, calcium nitrate, barium nitrate, and the like are preferably used.

These raw materials may be used in a solid form or in an aqueous solution state.

Next, the liquid mixture containing the zinc oxide which is coated with silicon oxide, which is generated by the substitution step, is separated into solid and liquid by the method of normal pressure filtration, reduced pressure filtration, pressurized filtration, centrifugal separation or the like. The obtained solid substance is cleaned using a solvent such as water or the like, thereby obtaining zinc oxide which is coated with silicon oxide.

Meanwhile, in order to further decrease the amount of the alkali metal included in the obtained zinc oxide which is coated with silicon oxide, it is preferable, after the solid-liquid separation is performed, to carry out again a substitution step wherein the obtained zinc oxide which is coated with silicon oxide and at least one element selected from a group consisting of Mg, Ca, and Ba are mixed in a solution including water so that the alkali metal included in the zinc oxide which is coated with silicon oxide is substituted with the at least one element selected from a group consisting of Mg, Ca, and Ba. It is more preferable that this substitution step is repeated multiple times.

The zinc oxide which is coated with silicon oxide obtained in the above-described manner includes water and thus is preferably dried in order to remove the water.

The drying temperature is not particularly limited; however, generally, the zinc oxide which is coated with silicon oxide is preferably dried at a temperature of 100° C. or higher. In addition, in a case in which the zinc oxide which is coated with silicon oxide is preferably dried at a low temperature of 80° C. or lower, the zinc oxide which is coated with silicon oxide is preferably dried at a reduced pressure.

(2) Second Embodiment

The method of manufacturing zinc oxide which is coated with silicon oxide of the present embodiment includes the following steps. That is, the manufacturing method is provided which includes: preparing a water-based suspension which includes zinc oxide particles and alkali metal silicate by adding a zinc oxide water-based suspension which includes zinc oxide particles to an alkali metal silicate aqueous solution which includes alkali metal silicate;

adding an acid to the water-based suspension; and adding an aqueous solution which includes at least one selected from a group consisting of magnesium salts, calcium salts and barium salts to the water-based suspension to which the acid has been added to perform ion-exchange wherein alkali metal ions derived from the alkali metal silicate is exchanged with ions of at least one selected from a group consisting of Mg, Ca, and Ba.

Meanwhile, in order to reduce the elution of zinc ions, before or after the ion-exchange step, zinc oxide coated with silicon oxide which includes an alkali metal may be allowed to react with a silicon (Si) alkoxide or a titanium (Ti) alkoxide, so that a silicon oxide coating, a titanium oxide coating or a composite coating which includes silicon oxide and titanium oxide is further formed on the silicon oxide coating provide on the zinc oxide.

Examples of the silicon (Si) alkoxide include tetramethyl orthosilicate (TMOS), tetraethyl orthosilicate (TEOS), silicate oligomers, and the like. In addition, examples of the titanium (Ti) alkoxide include titanium ethoxide, titanium isopropoxide, titanium butoxide (titaniumtetra-n-butoxide), and the like.

Next, a preferred example of the method for manufacturing zinc oxide which is coated with silicon oxide of the present embodiment will be described in detail.

In the preparation of the zinc oxide water-based suspension, zinc oxide particles and water are mixed together, and then the zinc oxide particles are dispersed in the water, thereby preparing a zinc oxide water-based suspension including zinc oxide particles.

A method for dispersing zinc oxide particles in water is not particularly limited, and, for example, an ultrasonic dispersion method, a stirring method, or the like is used.

Next, the zinc oxide water-base suspension is added to an aqueous solution of alkali metal silicate including alkali metal silicate, and the components are stirred, thereby preparing a water-based suspension including zinc oxide particles and alkali metal silicate.

The content of sodium silicate in the aqueous solution of alkali metal silicate that is added thereto is preferably in a range of 1% by mass or more and 30% by mass or less, more preferably in a range of 5% by mass or more and 30% by mass or less, and still more preferably in a range of 5% by mass or more and 20% by mass or less of the total mass of the zinc oxide particles in the zinc oxide water-based suspension in terms of silicon oxide.

As the alkali metal silicate, for example, sodium silicate or the like is used.

Next, the above-described water-based suspension is preferably reacted while being heated to 40° C. to 100° C. and more preferably reacted while being heated to 50° C. to 70° C.

Furthermore, an acid such as a diluted acid is gradually added to the water-based suspension under stirring so as to adjust the pH to be 5 to 9, thereby obtaining a water-based suspension of zinc oxide coated with silicon oxide. After that, an aqueous solution including at least one salt selected from a group consisting of magnesium salts, calcium salts, and barium salts is added to the water-based suspension. After that, an ion-exchange reaction is performed for one hour to 24 hours under stirring.

When the aqueous solution including at least one salt selected from a group consisting of magnesium salts, calcium salts, and barium salts is added to the water-based suspension under stirring, at least one kind of ions selected from a group consisting of the alkali metal (for example, sodium ions ($Na^+$)), magnesium ions ($Mg^{2+}$) derived from magnesium salts, calcium ions ($Ca^{2+}$) derived from calcium salts, and barium ions ($Ba^{2+}$) derived from barium salts in the silicon oxide coatings are exchanged. The alkali metal in the silicon oxide coatings is likely to liberate in water. However, magnesium, calcium, and barium in the silicon oxide coatings barely liberate. Therefore, the ion-exchange reaction proceeds.

The concentration of at least one salt selected from a group consisting of magnesium salts, calcium salts, and barium salts in the aqueous solution including at least one salt selected from a group consisting of magnesium salts, calcium salts, and barium salts is not particularly limited. In order to perform ion-exchange wherein alkali metal ions that are liberated and eluted from the alkali metal silicate are exchanged with at least one kind of ions selected from a group of Mg, Ca, and Ba, it is preferable that the concentration of said salt is preferably equal to or greater than the sum of the molar equivalents of alkali metal ions derived from the alkali metal silicate and other alkali metal ions.

Examples of the magnesium salt include magnesium chloride, magnesium sulfate, magnesium nitrate, and the like.

Examples of the calcium salt include calcium chloride, calcium nitrate, and the like.

Examples of the barium salt include barium nitrate and the like.

Next, the above-described water-based suspension is separated into solid and liquid using a centrifugal separator, a filter press, a rotary filter, or the like, and the obtained solid substance is cleaned with water. Therefore, zinc oxide particles coated with silicon oxide coatings containing at least one selected from Mg, Ca, and Ba are obtained.

Next, the solid substance is dried. A thermal treatment (calcination) is carried out on the dried substance at 200° C. or higher and lower than 600° C., thereby producing zinc oxide which is coated with silicon oxide of the present embodiment.

Meanwhile, before the calcination, a step of forming silicon oxide coatings having a higher condensation degree by adding the solid substance, at least one of alkoxysilane and oligomers of alkoxysilane which are decamers or lower, a catalyst, and water thereto and reacting the components for 30 minutes or longer and 24 hours under stirring may be provided.

"Composition which Includes Zinc Oxide Coated with Silicon Oxide"

A composition which includes zinc oxide coated with silicon oxide of the present embodiment comprises the zinc oxide which is coated with silicon oxide of the present embodiment and a solvent.

In the composition which includes zinc oxide coated with silicon oxide of the present embodiment, the average particle diameter of the zinc oxide which is coated with silicon oxide can be arbitrarily selected and is preferably 2 nm or more and 500 nm or less, more preferably 5 nm or more and 400 nm or less, and still more preferably 10 nm or more and 400 nm or less.

Here, the reasons for limiting the average particle diameter of the zinc oxide which is coated with silicon oxide in the above-described range are explained below. When the average particle diameter thereof is less than 2 nm, the particle diameters are too small, and thus the surface energy of zinc oxide which is coated with silicon oxide becomes high, and therefore the zinc oxide which is coated with silicon oxide particles easily form aggregate thereof. Accordingly, it becomes difficult to maintain a desired shape and size thereof. On the other hand, when the particle diameters exceed 500 nm, the transparency of the zinc oxide which is coated with silicon oxide is likely to degrade, and, in a case in which the composition which includes zinc oxide coated with silicon oxide is used in cosmetics and the like, there is a concern that transparency in the visible light range may be impaired or the feeling of using cosmetics and the like may deteriorate due to the generation of creak or the like.

The average dispersed particle diameter of the zinc oxide which is coated with silicon oxide in the composition which includes zinc oxide coated with silicon oxide of the present embodiment is preferably 10 nm or more and 1 μm or less. The average dispersed particle diameter thereof is more preferably 20 nm or more and 800 nm or less and still more preferably 25 nm or more and 500 nm or less. When the average dispersed particle diameter of the zinc oxide which is coated with silicon oxide is less than 10 nm, the crystallinity of the zinc oxide which is coated with silicon oxide decreases, and consequently, there is a concern that sufficient ultraviolet-shielding properties may not be exhibited. On the other hand, when the average dispersed particle diameter of the zinc oxide which is coated with silicon oxide exceeds 1 μm, glares, creak, and the like are generated, and thus there is a concern that, when the composition is formulated into cosmetics, the feeling of using cosmetics may deteriorate, and there is a concern that dispersion stability may degrade and stable compositions may not be obtained. Meanwhile, in the present invention, the dispersed particle diameter refers to the particle diameter of dispersed aggregate of multiple gathered zinc oxides coated with silicon oxide particles.

The content rate of the zinc oxide which is coated with silicon oxide in the composition which includes zinc oxide coated with silicon oxide of the present embodiment may be appropriately adjusted in order to obtain desired ultraviolet-shielding performance and is not particularly limited. The content rate thereof is preferably 1% by mass or more and 80% by mass or less, more preferably 5% by mass or more and 70% by mass or less, and still more preferably 10% by mass or more and 60% by mass or less.

Here, the content rate of the zinc oxide which is coated with silicon oxide is said to be preferably 1% by mass or more and 80% by mass or less. The reasons therefor are as described below. When the content rate of the zinc oxide which is coated with silicon oxide is less than 1% by mass, it becomes impossible for the composition which includes zinc oxide coated with silicon oxide to exhibit a sufficient ultraviolet-shielding function. As a result, when the composition which includes zinc oxide coated with silicon oxide is formulated into cosmetics, it is necessary to add a large amount of the composition which includes zinc oxide coated with silicon oxide in order to exhibit a desired ultraviolet-shielding function, and there is a concern that the manufacturing cost may increase, which is not preferable. On the other hand, when the content rate of the zinc oxide which is coated with silicon oxide exceeds 80% by mass, the viscous properties of the composition which includes zinc oxide coated with silicon oxide increase, and thus the dispersion stability of the zinc oxide which is coated with silicon oxide degrades, and there is a concern that it may become easy for the zinc oxide which is coated with silicon oxide to settle, which is not preferable.

A solvent that is used in the composition which includes zinc oxide coated with silicon oxide of the present embodiment is not particularly limited as long as the solvent is capable of dispersing the zinc oxide which is coated with silicon oxide. For example, it is possible to use water, alcohols such as methanol, ethanol, 1-propanol, 2-propanol, 1-butanol, 2-butanol, octanol, and glycerin;

esters such as ethyl acetate, butyl acetate, ethyl lactate, propylene glycol monomethyl ether acetate, propylene glycol monoethyl ether acetate, and γ-butyrolactone; and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether. These solvents may be used singly or two or more solvents may be used in a mixed form.

In addition, as an example of other solvents that can be used in the composition which includes zinc oxide coated with silicon oxide of the present embodiment, ketones such as acetone, methyl ethyl ketone, methyl isobutyl ketone, acetyl acetone, and cyclohexanone;

aromatic hydrocarbons such as benzene, toluene, xylene, and ethyl benzene;

cyclic hydrocarbons such as cyclohexane;

amides such as dimethyl formamide, N,N-dimethylacetoacetamide, and N-methyl pyrrolidone; and chain-like polysiloxanes such as dimethyl polysiloxane, methyl phenyl polysiloxane, and diphenyl polysiloxane are also preferably used.

In addition, cyclic polysiloxane such as octamethyl cyclotetrasiloxane, decamethyl cyclopentasiloxane, and dodecamethyl cyclohexanesiloxane; and denatured polysiloxanes such as amino-denatured polysiloxane, polyether-denatured polysiloxane, alkyl-denatured polysiloxane, and fluorine-denatured polysiloxane are also preferably used.

These solvents may be used singly or two or more solvents may be used in a mixed form.

The composition which includes zinc oxide coated with silicon oxide of the present embodiment may include generally-used additives such as a dispersant, a stabilizer, a water-soluble binder, and a viscosity improver as long as the characteristics are not impaired.

As the dispersant, silane coupling agents such as anionic surfactants, cationic surfactants, ampholytic surfactants, nonionic surfactants, organoalkoxysilane, or organochlorosilane, and denatured silicone such as polyether-denatured silicone and amino-denatured silicone are preferably used. The kind or amount of the dispersant may be appropriately selected depending on the particle diameter of composite particles or the kind of an intended dispersion medium, and the dispersant may be used singly, or two or more dispersants may be used in a mixed form.

As the water-soluble binder, it is possible to use, for example, polyvinyl alcohol (PVA), polyvinyl pyrrolidone, hydroxycellulose, polyacrylic acid, or the like.

In a case in which the composition which includes zinc oxide coated with silicon oxide of the present embodiment is applied to cosmetics, the viscosity improver is not particularly limited as long as the viscosity can be used in cosmetics. As the viscosity improver, natural water-soluble polymers such as gelatin, casein, collagen, hyaluronic acid, albumin, and starch, semisynthetic polymers such as methyl cellulose, ethyl cellulose, methyl hydroxy propyl cellulose, carboxymethyl cellulose, hydroxymethyl cellulose, hydroxypropyl cellulose, sodium carboxymethyl cellulose, and propylene glycol alginate esters, synthetic polymers such as polyvinyl alcohols, polyvinyl pyrrolidone, carbomers (carboxyvinyl polymers), polyacrylates, and polyethylene oxides, inorganic minerals such as bentonite, laponite, and hectorite, and the like are preferably used. The viscosity improver may be used singly, or two or more viscosity improvers may be used in a mixed form.

Among these viscosity improvers, synthetic polymers are preferred, and carbomers (carboxyvinyl polymers) are more preferred.

Here, in a case in which a carbomer is used as the viscosity improver, the content rate of the carbomer in the composition which includes zinc oxide coated with silicon oxide of the present embodiment is preferably 0.0001% by mass or more and 10% by mass or less and more preferably 0.01% by mass or more and 1% by mass or less.

When the content rate of the carbomer in the composition which includes zinc oxide coated with silicon oxide of the present embodiment is less than 0.0001% by mass, there is a concern that the viscosity-improving effect cannot be obtained. On the other hand, when the content rate of the carbomer exceeds 10% by mass, the viscosity of the composition which includes zinc oxide coated with silicon oxide excessively increases, which is not preferable from the viewpoint of using the composition.

In addition, in a case in which a carbomer is used as the viscosity improver, the hydrogen-ion exponent (pH) in the silicon-oxide-coated zinc-oxide-containing composition is preferably 5 or more and 9 or less, more preferably 6 or more and 9 or less, and still more preferably 7 or more and 9 or less. When the pH in the composition which includes zinc oxide coated with silicon oxide of the present embodiment is within the above-described range, it is possible to suppress the temporal change of the viscosity and the like.

Meanwhile, the above-described carbomer (carboxyvinyl polymer) is widely used as a viscosity improver for water-based cosmetics. However, since the viscosity is improved (gelatified) using an interaction between carboxyl groups or between carboxylate groups, when zinc ions are present, the network structure of the carbomer is broken, and the viscous properties cannot be maintained to be constant. Therefore, when several % by mass of zinc oxide is mixed with an aqueous solution of the carbomer having an adjusted viscosity, the viscosity begins to decrease within several hours. In addition, even in a case in which zinc oxide having the surface activity suppressed by being coated with an inorganic oxide or a resin is used, in many cases, the viscosity begins to decrease or phases begin to be divided within several hours to several days. Therefore, in a case in which the carbomer and zinc oxide are jointly used, there is a problem in that it is necessary to suppress or reduce the decrease in the viscosity of a mixture including both.

In addition, in a case in which a decrease in the viscosity of the aqueous solution of the carbomer is suppressed using zinc oxide of the related art which has the surface activity suppressed by being coated with an inorganic oxide or a resin, there is a problem in that the degree of viscosity decrease after a certain period of time is greater than the degree of viscosity decrease in the initial phase in many cases.

The viscosity decrease in the initial phase can be coped with by adjusting the viscosity of the aqueous solution of the carbomer to be high in advance. However, when the viscosity changes in a middle phase after a certain period of time, the properties of cosmetics change in the distribution phase, and temporal stability is impaired. Particularly, zinc oxide on which a surface treatment is carried out using an inorganic oxide or a resin has a certain degree of elution-suppressing effect, there has been a concern that zinc ions may gradually elute over a long or middle period of time.

In addition, in the related art, there are only a small number of reported examples regarding the viscosity change in compositions including the carbomer, and, even in the existing reported examples, what has been confirmed is that viscosity change can be suppressed for approximately seven days at room temperature.

Here, a composition having excellent quality stability can be obtained, when the zinc oxide coated with silicon oxide of the present embodiment is used in which the decomposition rate of Brilliant Blue caused by the photocatalytic activity of zinc oxide particles is 3% or less, and abundance ratios satisfy $Q^3+Q^4 \geq 0.6$ and $Q^4/(Q^3+Q^4) \geq 0.5$ when the abundance ratio of silicon in the silicon oxide coatings in a $Q^3$ environment is denoted by $Q^3$, and the abundance ratio of silicon in the silicon oxide coatings in a $Q^4$ environment is denoted by $Q^4$. That is, in the composition which includes zinc oxide coated with silicon oxide of the present embodiment, since zinc oxide which is coated with silicon oxide which has a stronger zinc elution-suppressing effect than zinc oxide coated with an inorganic oxide or a resin of the related art is used, even when the carbomer is used as the viscosity improver, compositions in which the viscosity decreases only slightly over time and the quality stability is excellent can be obtained.

In the composition which includes zinc oxide coated with silicon oxide of the present embodiment, the value obtained by dividing the viscosity in the case of being stored under acceleration conditions, for example, the viscosity measured after 300 hours in the case of being stored at 40° C. by the viscosity after a viscosity decrease under the initial conditions, for example, the viscosity measured after 15 hours at the above-described temperature is preferably 0.8 or more and 1.2 or less.

As described above, when the value obtained by dividing the viscosity under acceleration conditions, that is, after 300 hours by the viscosity after the initial viscosity decrease is set in the above-described range, it is possible to maintain the viscosity of the composition which includes zinc oxide coated with silicon oxide of the present embodiment for a long or middle period of time. The above-described compositions can be obtained by controlling the conditions described in the present invention.

In a case in which the content rate of the zinc oxide which is coated with silicon oxide in the composition which includes zinc oxide coated with silicon oxide of the present embodiment is set to 15% by mass, and a 32 μm-thick coating is formed using the composition, the light transmittance of the coating at a wavelength of 450 nm is preferably 50% or more, more preferably 60% or more, and still more preferably 70% or more.

The transmittance can be obtained by applying the composition which includes zinc oxide coated with silicon oxide, wherein 15% by mass of the zinc oxide coated with silicon oxide is included, onto a silica substrate using a bar coater so as to form a 32 μm-thick coating, and measuring the spectral transmittance of the coating using an SPF analyzer UV-1000S (manufactured by Labsphere, Inc.). At this time, a component of the composition other than the zinc oxide which is coated with silicon oxide may be, for example, a solvent such as water.

The method of manufacturing a composition which includes zinc oxide coated with silicon oxide of the present embodiment is not particularly limited as long as it is possible to disperse the zinc oxide which is coated with silicon oxide in the above-described solvent.

As a dispersion method that is used for the above-described dispersion, a well-known dispersion method can be used. For example, it is possible to preferably use dispersion methods in which, in addition to a stirrer, a bead mill in which zirconia beads are used, a ball mill, a homogenizer, an ultrasonic disperser, a kneader, a three-roll mill, a rotation and revolution mixer, or the like are used.

The duration of the dispersion treatment is not particularly limited as long as the zinc oxide which is coated with silicon oxide is evenly dispersed in the solvent.

Next, as specific examples of the composition which includes zinc oxide coated with silicon oxide of the present embodiment, (a) zinc oxide which is coated with silicon oxide-containing silicone resin-based composition in which zinc oxide which is coated with silicon oxide is dispersed in a silicone resin which is a water-insoluble dispersion medium and (b) zinc oxide which is coated with silicon oxide-containing water-based composition in which zinc oxide which is coated with silicon oxide is dispersed in water will be described respectively.

(Zinc Oxide which is Coated with Silicon Oxide-Containing Silicone Resin-Based Composition)

The zinc oxide which is coated with silicon oxide-containing silicone resin-based composition is a silicone resin-based composition in which the above-described zinc oxide which is coated with silicon oxide is dispersed in a silicone resin. In this composition, the content rate of the zinc oxide which is coated with silicon oxide is preferably set to 1% by mass or more and 80% by mass or less, more preferably set to 20% by mass or more and 70% by mass or less, and still more preferably set to 30% by mass or more and 60% by mass or less.

The zinc oxide which is coated with silicon oxide may be formed by carrying out a surface treatment on the surface thereof using a silicone resin.

When a surface treatment is carried out on the zinc oxide which is coated with silicon oxide using a silicone resin, the affinity to oil phases, particularly, silicone oils increases. Therefore, it becomes easier to formulate the zinc oxide which is coated with silicon oxide into water-in-oil type (W/O-type) or oil-in-water-type (O/W) cosmetics.

That is, when water-in-oil type (W/O-type) or oil-in-water-type (O/W) cosmetics are produced by formulating the zinc oxide which is coated with silicon oxide on which a surface treatment is carried out using a silicone resin into oil phases, it is possible to suppress the elution of zinc ions in the water-in-oil type (W/O-type) or oil-in-water-type (O/W) cosmetics.

The silicone resin that is used in the surface treatment is not particularly limited as long as the silicone resin can be used as cosmetics. Examples thereof include methyl hydrogen polysiloxane, dimethyl polysiloxane, methicone, hydrogen dimethicone, triethoxysilyl ethyl polydimethylsiloxyethyl dimethicone, triethoxysilyl ethyl polydimethylsiloxyethylhexyl dimethicone, (acrylate/tridecyl acrylate/triethoxysilylpropyl methacrylate/dimethicone methacrylate) copolymers, triethoxycaprylylsilane, and the like. These silicone resins may be used singly, two or more silicone resins may be used in a mixed form, or a copolymer thereof may be used.

The silicone resin may be a cyclic silicone resin or a linear silicone resin having a structural skeleton represented by Formula (2) below and is not particularly limited.

$$(-Si(CH_3)_2O-)_X \quad (2)$$

(In Formula (2), X is in a range of 1 to 2,000.)

When the value of X is set in the above-described range, it becomes easy to mix the silicone resin with the zinc oxide which is coated with silicon oxide, which is preferable.

Examples of the silicone resin include dimethyl polysiloxane, methyl phenyl polysiloxane, hexamethyl cyclotrisiloxane, octamethyl cyclotetrasiloxane, decamethyl pentasiloxane, methyl trimethicone, and the like.

The zinc oxide which is coated with silicon oxide-containing silicone resin-based composition may contain a dispersant.

Examples of the dispersant include polyether-denatured silicone, polyglycerin-denatured silicone, amino-denatured silicone, phenyl-denatured silicone, alkyl-denatured silicone, carbinol-denatured silicone, dimethyl silicone, and the like.

The amount of the dispersant added can be arbitrarily selected and is preferably in a range of 1% by mass or more and 50% by mass or less of the mass of the zinc oxide which is coated with silicon oxide in the zinc oxide which is coated with silicon oxide-containing silicone resin-based composition. For example, the amount of the dispersant added may be, for example, in a range of 3% by mass or more and 15% by mass or less, 10% by mass to 30% by mass, or the like as necessary.

When the amount of the dispersant added is adjusted in the above-described range, even in a case in which the zinc oxide which is coated with silicon oxide-containing silicone resin-based composition is used singly or a case in which the zinc oxide which is coated with silicon oxide-containing silicone resin-based composition is directly mixed with cosmetics, it is possible to ensure sufficient transparency in a case in which the cosmetics are applied and spread on skins.

In addition, in the zinc oxide which is coated with silicon oxide-containing silicone resin-based composition, natural oils, moisturizing agents, viscosity improvers, fragrance, preservatives, and the like may be further mixed as long as the characteristics are not impaired.

(Zinc Oxide which is Coated with Silicon Oxide-Containing Water-Based Composition)

The zinc oxide which is coated with silicon oxide-containing water-based composition is a water-based composition obtained by dispersing the zinc oxide which is coated with silicon oxide in a water-based dispersion medium including alcohols. In this composition, the content rate of the zinc oxide which is coated with silicon oxide is preferably 1% by mass or more and 80% by mass or less, more preferably 20% by mass or more and 70% by mass or less, and still more preferably 30% by mass or more and 60% by mass or less. The content of the water-based dispersion medium including alcohols is preferably in a range of 20% by mass to 99% by mass, more preferably in a range of 30% by mass to 80% by mass, and still more preferably in a range of 40% by mass to 70% by mass.

Here, the water-based dispersion medium including alcohols refers to a dispersion medium including alcohols and water. Examples of the alcohols include monovalent alcohols or polyvalent alcohols having 1 to 6 carbon atoms such as ethanol, 1-propanol, 2-propanol, 1-butanol, 2-butanol, octanol, glycerin, 1,3-butylene glycol, propylene glycol, and sorbitol. Among these, monovalent alcohols are preferred, and ethanol is particularly preferred.

In a case in which the zinc oxide which is coated with silicon oxide-containing water-based composition is constituted of the zinc oxide which is coated with silicon oxide and the water-based dispersion medium including alcohols, the content rate of the alcohols is preferably 5% by mass or more and 20% by mass or less and more preferably 10% by mass or more and 20% by mass or less.

Particularly, in a case in which the content rate of the alcohols is set to 5% by mass or more and 20% by mass or less, it is possible to improve the dispersibility and the temporal stability of the zinc oxide which is coated with silicon oxide in the water-based composition, which is preferable.

The zinc oxide which is coated with silicon oxide-containing water-based composition may further contain 0.001% by mass or more and 10% by mass or less, more preferably 0.005% by mass or more and 5% by mass or less, and still more preferably 0.01% by mass or more and 3% by mass or less of a water-soluble polymer. In this case, it is necessary to adjust the content rates of the respective components so that the total of the respective content rates of the zinc oxide which is coated with silicon oxide, the water-based dispersion medium including the alcohols, and the water-soluble polymer does not exceed 100% by mass.

In a case in which the zinc oxide which is coated with silicon oxide-containing water-based composition is applied to cosmetics, the water-soluble polymer in this water-based composition is not particularly limited as long as the water-soluble polymer can be used for the application of cosmetics. Examples thereof include gum arabic, sodium alginate, casein, carrageenan, galactan, carboxyvinyl polymers, carboxy methyl cellulose, sodium carboxy methyl cellulose, carboxymethyl starch, agar, xanthan gum, quince seed, guar gum, collagen, gelatin, cellulose, dextran, dextrin, gum tragacanth, hydroxyethyl cellulose, hydroxypropyl cellulose, sodium hyaluronate pectin, pullulan, methyl cellulose, methyl hydroxypropyl cellulose, and the like. These water-soluble polymers may be used singly, or two or more water-soluble polymers may be used in a mixed form.

This water-soluble polymer plays a role of a dispersant and a viscosity adjuster and also plays a role of improving dispersibility and temporal stability in the zinc oxide which is coated with silicon oxide-containing water-based composition
when added to the water-based composition.

In a case in which the zinc oxide which is coated with silicon oxide-containing water-based composition
includes the water-soluble polymer, the content rate of the alcohols is preferably 5% by mass or more and 20% by mass or less and more preferably 15% by mass or more and 20% by mass or less.

Here, in a case in which the zinc oxide which is coated with silicon oxide-containing water-based composition
includes the water-soluble polymer, the content rate of the alcohols is set to 5% by mass or more and 20% by mass or less. The reasons therefor are as described below. That is, in a case in which the content rate is less than 5% by mass, the content of the alcohols is too low, and thus the water-soluble polymer is not capable of evenly infiltrating into the alcohols and unevenly swells due to moisture. As a result, the dispersibility of the zinc oxide which is coated with silicon oxide degrades, it becomes difficult to handle the zinc oxide which is coated with silicon oxide, and furthermore, the temporal stability of the zinc oxide which is coated with silicon oxide-containing water-based composition degrades, which is not preferable. In addition, when the content rate exceeds 20% by mass, the viscosity of the entire zinc oxide which is coated with silicon oxide-containing water-based composition increases. As a result, the dispersion stability of the zinc oxide which is coated with silicon oxide degrades, and the temporal stability of the zinc oxide which is coated with silicon oxide-containing water-based composition degrades, which is not preferable.

The zinc oxide which is coated with silicon oxide-containing water-based composition can be obtained by mixing the above-described zinc oxide which is coated with silicon oxide with the water-based dispersion medium including the alcohols or the water-based dispersion medium including the alcohols and the water-soluble polymer, then, mixing water thereinto as necessary, and dispersing the components. The amount of the water in the composition may be appropriately adjusted, and, when the dispersion stability and temporal stability of the zinc oxide which is coated with silicon oxide are taken into account, the amount thereof is preferably in a range of 15% by mass or more and 94% by mass or less. A preferred amount thereof may be selected in this range as necessary.

When the amount of the water is adjusted to be in the above-described range, even when the zinc oxide which is coated with silicon oxide-containing water-based composition is used singly or is mixed with cosmetics, it is possible to obtain zinc oxide which is coated with silicon oxide-containing water-based compositions capable of ensuring sufficient transparency in a case in which the cosmetics are applied and spread on skins.

[Cosmetic]

A cosmetic of the present embodiment contains at least one of the zinc oxide which is coated with silicon oxide and the composition which includes zinc oxide coated with silicon oxide in a base material thereof.

In a case in which zinc oxide which is coated with silicon oxide is used for ultraviolet-shielding use, it is preferable to use zinc oxide which is coated with silicon oxide having an average particle diameter of 2 nm or more and 500 nm or less as the zinc oxide which is coated with silicon oxide.

In addition, in a case in which a composition which includes zinc oxide coated with silicon oxide is used for ultraviolet-shielding use, it is preferable to use a composition which includes zinc oxide coated with silicon oxide including zinc oxide which is coated with silicon oxide having an average particle diameter of 2 nm or more and 500 nm or less as the composition which includes zinc oxide coated with silicon oxide.

The content rate of the zinc oxide which is coated with silicon oxide in the cosmetic in which either or both the zinc oxide which is coated with silicon oxide and the composition which includes zinc oxide coated with silicon oxide are used may be appropriately adjusted. The content of the zinc oxide which is coated with silicon oxide is preferably 1% by mass or more and 60% by mass or less of the mass of the entire cosmetic. When the zinc oxide which is coated with silicon oxide is contained in the above-described range, it is possible to endure sufficient transparency and, furthermore, to obtain cosmetics which are not sticky and have an excellent feeling of use.

The cosmetic of the present embodiment may contain organic ultraviolet-shielding agents, inorganic ultraviolet-shielding agents, additives, and the like as long as the effects of the present invention are not impaired.

Examples of the organic ultraviolet-shielding agents include anthranilates, cinnamic acid derivatives, salicylic acid derivatives, camphor derivatives, benzophenone derivatives, β,β'-diphenylacrylate derivatives, benzotriazol derivatives, benzalmalonate derivatives, benzoimidazole derivatives, imidazolines, bisbenzoazoryl derivatives, p-amino benzoic acid (PABA) derivatives, methylene bis (hydroxyphenylbenzotriazole) derivatives, and the like, and it is possible to select and use at least one organic ultraviolet-shielding agent selected from a group thereof.

In addition, examples of the inorganic ultraviolet-shielding agents include oxides other than zinc oxide such as titanium oxide and cerium oxide, and it is possible to select and use at least one inorganic ultraviolet-shielding agent selected from a group thereof.

The cosmetic of the present embodiment can be obtained by formulating the zinc oxide which is coated with silicon oxide into a base material such as emulsions, creams, foundations, lipsticks, blushers, eye shadows as in the related art.

Furthermore, when the zinc oxide which is coated with silicon oxide of the present embodiment is formulated into water-based cosmetics such as skin lotions or sunscreens, the formulation of which is difficult in the related art, it is possible to obtain water-based cosmetics which are excellent in terms of ultraviolet-shielding properties, transparency, and feeling of use.

Furthermore, when this cosmetic is used as a component of cosmetic products, it is possible to provide a variety of cosmetic products such as skin care cosmetic products, makeup cosmetic products, and body care cosmetic products which are excellent in terms of ultraviolet-shielding properties, transparency, and feeling of use. Particularly, the cosmetic is preferable for the sun screening and the like of body care products requiring ultraviolet-shielding performance.

As described above, the zinc oxide which is coated with silicon oxide of the present embodiment comprises at least one element selected from a group consisting of Mg, Ca, and Ba. As a result, even in a case in which the zinc oxide which is coated with silicon oxide is applied to water-based materials such as water-based cosmetics, it is possible to suppress a change in the hydrogen-ion exponents (pH) of the water-based materials. Therefore, it is possible to maintain the stability of the quality of the water-based materials.

Furthermore, dense and homogeneous silicon oxide coatings can be obtained when the decomposition rate of Brilliant Blue caused by the photocatalytic activity of the coated zinc oxide particles is 3% or less, and abundance ratios satisfy $Q^3+Q^4 \geq 0.6$ and $Q^4/(Q^3+Q^4) \geq 0.5$ wherein the abundance ratio of silicon in the silicon oxide coatings in a $Q^3$ environment is denoted by $Q^3$, and the abundance ratio in the silicon oxide coatings in a $Q^4$ environment is denoted by $Q^4$. As a result, it is possible to further suppress the elution of zinc ions.

In addition, the zinc oxide which is coated with silicon oxide and the water-based composition including the carbomer are capable of suppressing viscosity decrease over time.

The method of manufacturing zinc oxide which is coated with silicon oxide of the present embodiment includes a step of mixing, in a solution including water, at least one element selected from a group consisting of Mg, Ca, and Ba and zinc oxide which is coated with silicon oxide containing an alkali metal and replacing the alkali metal, which is included in the zinc oxide coated with silicon oxide, to the at least one element selected from a group consisting of Mg, Ca, and Ba. As a result, it is possible to reduce the amount of the alkali metal and to add at least one element selected from a group consisting of Mg, Ca, and Ba to the zinc oxide which is coated with silicon oxide. Therefore, even in a case in which the method is applied to water-based materials such as water-based cosmetics, it is possible to suppress a change in the hydrogen-ion exponents (pH) of the water-based materials. As a result, it is possible to easily produce zinc oxide which is coated with silicon oxide capable of maintaining the stability of the quality of water-based materials at low costs.

The method of manufacturing zinc oxide which is coated with silicon oxide of the present embodiment includes the following steps. That is, the manufacturing method includes:

preparing a water-based suspension which includes zinc oxide particles and alkali metal silicate by adding a zinc oxide water-based suspension which includes zinc oxide particles to an alkali metal silicate aqueous solution which includes alkali metal silicate;

adding an acid to the water-based suspension; and adding an aqueous solution which includes at least one selected from a group consisting of magnesium salts, calcium salts and barium salts to the water-based suspension to which the acid has been added to perform ion-exchange wherein alkali metal ions derived from the alkali metal silicate is exchanged with ions of at least one selected from a group consisting of Mg, Ca, and Ba. Therefore, even in a case in which the method is applied to water-based materials such as water-based cosmetics, it is possible to suppress a change in the hydrogen-ion exponents (pH) of the water-based materials, and therefore, it is possible to easily produce zinc oxide which is coated with silicon oxide capable of maintaining the stability of the quality of water-based materials at low costs.

Since the composition which includes zinc oxide coated with silicon oxide of the present embodiment contains the zinc oxide which is coated with silicon oxide of the present embodiment, even in a case in which the composition which includes zinc oxide coated with silicon oxide is applied to not only oil-based materials such as water-in-oil (W/O)-type materials but also water-based materials, it is possible to suppress a change in the hydrogen-ion exponents (pH) of the water-based materials. Therefore, it is possible to maintain the stability of qualities.

Since the cosmetic of the present embodiment contains the zinc oxide which is coated with silicon oxide of the present embodiment in the base material thereof, even in a case in which the cosmetic is applied to not only oil-based cosmetics such as water-in-oil (W/O)-type materials but also water-based materials, it is possible to suppress a change in the hydrogen-ion exponents (pH) of the cosmetics. Therefore, it is possible to suppress the degradation of performance as cosmetics, discoloration, an increase in the viscosity, and the like, which are all caused by a change in the hydrogen-ion exponent (pH) and to maintain the stability of qualities.

EXAMPLES

Hereinafter, preferred examples of the present invention will be specifically described using Examples 1 to 8 and Comparative Examples 1 to 5, but the present invention is not limited to the following examples.

Example 1

Zinc oxide particles (the average particle diameter of 35 nm; manufactured by Sumitomo Osaka Cement Co., Ltd.) and water were mixed together, and then, ultrasonic dispersion was carried out, thereby preparing a zinc oxide water-based suspension in which the content rate of zinc oxide was 20% by mass.

Next, this zinc oxide water-based suspension was added to an aqueous solution of silicate soda including 20% by mass of silicate soda of the mass of the zinc oxide particles in the zinc oxide suspension in terms of silicon oxide and was strongly stirred, thereby producing a suspension.

Next, this suspension was heated to 60° C., and a diluted acid was gradually added to the suspension under stirring so as to adjust the pH to be 6.5 to 7. After that, the suspension was left to stand for two hours, then, furthermore, the same mass of an aqueous solution of calcium chloride (25% by mass of calcium chloride dihydrate) as the mass of the zinc oxide particles in the suspension was added thereto and stirred, and the suspension was left to stand for additional two hours.

Next, this suspension was separated into solid and liquid using a centrifugal separator, and the obtained solid substance was cleaned with water. After that, the solid substance was dried at 150° C., and furthermore, a thermal treatment (calcination) was carried out at 500° C. for two hours, thereby producing zinc oxide which is coated with silicon oxide of Example 1.

Example 2

Zinc oxide which is coated with silicon oxide was produced according to Example 1.

Next, this zinc oxide which is coated with silicon oxide and 2-propanol were mixed together, and then, ultrasonic dispersion was carried out, thereby preparing a zinc oxide which is coated with silicon oxide 2-propanol suspension in which the content rate of zinc oxide which is coated with silicon oxide was 10% by mass.

Next, this suspension was heated to 60° C., ammonia water and water were added to the suspension under stirring so as to adjust the pH to be 10 to 11. Meanwhile, the amount of water added was set to be 120% by mass of tetramethoxysilane in a tetramethoxysilane 2-propanol solution that was added afterwards.

Furthermore, the tetramethoxysilane 2-propanol solution was slowly added dropwise to this suspension so that the amount of tetramethoxysilane added dropwise reached 15% by mass of the total mass of the zinc oxide in terms of silicon oxide and was continuously stirred for six hours.

After the end of the reaction, this suspension was separated into solid and liquid using a centrifugal separator, and the obtained solid substance was dried at 120° C. Next, a thermal treatment (calcination) was carried out on this dried substance at 500° C. for two hours, thereby producing zinc oxide which is coated with silicon oxide of Example 2.

Example 3

Zinc oxide which is coated with silicon oxide was produced according to Example 1.

Next, this zinc oxide which is coated with silicon oxide and 2-propanol were mixed together, and then, ultrasonic dispersion was carried out, thereby preparing a zinc oxide which is coated with silicon oxide 2-propanol suspension in which the content rate of zinc oxide which is coated with silicon oxide was 10% by mass.

Next, this suspension was heated to 60° C., ammonia water and water were added to the suspension under stirring so as to adjust the pH to be 10 to 11. Meanwhile, the amount of water added was set to be 120% by mass of tetramethoxysilane in a tetramethoxysilane 2-propanol solution that was added afterwards.

Furthermore, the tetramethoxysilane 2-propanol solution was slowly added dropwise to this suspension so that the amount of tetramethoxysilane added dropwise reached 15% by mass of the total mass of the zinc oxide in terms of silicon oxide and was continuously stirred for six hours.

After the end of the reaction, this suspension was separated into solid and liquid using a centrifugal separator, the obtained solid substance was dried at 120° C., a thermal treatment (calcination) was carried out at 500° C. for two hours, thereby producing zinc oxide which is coated with silicon oxide.

Next, this zinc oxide which is coated with silicon oxide and water were mixed together, and then, ultrasonic dispersion was carried out, thereby preparing a zinc oxide which is coated with silicon oxide water-based suspension in which the content rate of zinc oxide which is coated with silicon oxide was 10% by mass.

Next, the same mass of an aqueous solution of calcium chloride (25% by mass of calcium chloride dihydrate) as the mass of the zinc oxide which is coated with silicon oxide in the suspension was added thereto and stirred, and the suspension was left to stand for two hours.

Next, this suspension was separated into solid and liquid using a centrifugal separator a total of three times, and the obtained solid substance was dried at 150° C., thereby producing zinc oxide which is coated with silicon oxide of Example 3.

Meanwhile, when solid-liquid separation was repeated, solid-liquid separation was carried out using a centrifugal separator under the same conditions, that is, the same concentration and the same mass of an aqueous solution as those of the aqueous solution of calcium chloride which had been initially used was added to the solid substance obtained by means of the solid-liquid separation was added thereto.

Meanwhile, a carbomer Ultrez 10 (manufactured by Nikko Chemicals Co., ltd.) (1.5 g) was dissolved in pure water, and then an aqueous solution of 10% by mass of sodium hydroxide was added dropwise thereto so as to adjust the pH, thereby producing an aqueous solution of the carbomer which included 1.5% by mass of the carbomer and had a pH of 7.5.

Next, after the aqueous solution of the carbomer and the zinc oxide which is coated with silicon oxide were mixed together in a mass ratio of 95:5 and then were stirred together, thereby obtaining a silicon-oxide-coated zinc-oxide-containing composition.

The viscosity of the composition was measured using a viscometer BII-type viscometer (manufactured by Toki Sangyo Co., Ltd.) on the basis of conditions of 20° C. and 30 rpm and was found to be 7.8 Pa·s. A predetermined amount of the composition was sampled, the sampled specimen was held at 40° C. using a temperature-constant tank, and the viscosity was measured every predetermined time on the basis of conditions of 20° C. and 30 rpm. The results of the viscosity are illustrated in FIG. 1.

Example 4

Zinc oxide particles (the average particle diameter of 35 nm; manufactured by Sumitomo Osaka Cement Co., Ltd.) and water were mixed together, and then, ultrasonic dispersion was carried out, thereby preparing a zinc oxide water-based suspension in which the concentration of zinc oxide was 50 g/L (5% by mass).

Next, this suspension was heated to 80° C., and an aqueous solution of sodium silicate was added to this suspension under stirring so as to be 10% by mass of zinc oxide in terms of silicon oxide, and the mixture was aged for 10 minutes.

Next, a diluted acid was added to the suspension under stirring over 60 minutes so as to adjust the pH to be 6.5, and the mixture was aged for 30 minutes.

Next, an aqueous solution of sodium aluminate was added to this suspension under stirring so as to be 5% by mass of the total mass of zinc oxide in terms of aluminum oxide, and the mixture was aged for 10 minutes.

Next, a diluted acid was added to the suspension under stirring over 10 minutes so as to adjust the pH to be 7.0, and the mixture was aged for 30 minutes.

Next, this suspension was separated into solid and liquid using a centrifugal separator, was cleaned with water, and the obtained solid substance was heated and dried at 130° C. for five hours. Next, the dried substance was crushed using a jet mill.

Next, this crushed product and water were mixed together, and then, ultrasonic dispersion was carried out, thereby preparing a zinc oxide which is coated with silicon oxide water-based suspension in which the content rate of zinc oxide which is coated with silicon oxide was 10% by mass.

Next, the same mass of an aqueous solution of calcium chloride (25% by mass of calcium chloride dihydrate) as the mass of the zinc oxide which is coated with silicon oxide in the suspension was added thereto and stirred, and the suspension was left to stand for two hours.

Next, this suspension was separated into solid and liquid using a centrifugal separator three times, and the obtained solid substance was dried at 150° C., thereby producing zinc oxide which is coated with silicon oxide of Example 4.

Meanwhile, when solid-liquid separation was repeated, solid-liquid separation was carried out using a centrifugal separator under the same conditions, that is, the same concentration and the same mass of an aqueous solution as those of the aqueous solution of calcium chloride which had been initially used was added to the solid substance obtained by means of the solid-liquid separation was added thereto.

Example 5

An aqueous solution of sodium silicate was added to zinc oxide particles (the average particle diameter of 35 nm; manufactured by Sumitomo Osaka Cement Co., Ltd.) so as to be 9% by mass of the zinc oxide particles in terms of silicon oxide and was strongly stirred, thereby producing a suspension. An acid such as a diluted acid was gradually added to this suspension under stirring so as to adjust the pH to be 7, and the mixture was left to stand for four hours. Then, an oxide of silicon was gradually precipitated on the surfaces of zinc oxide particles, and coatings were formed on the surfaces.

Next, this suspension was separated into solid and liquid using a centrifugal separator, was cleaned with water, and the obtained solid substance was heated and dried at 105° C. for 24 hours, thereby producing surface-reformed zinc oxide.

Next, this surface-reformed zinc oxide and water were mixed together, and then, ultrasonic dispersion was carried out, thereby preparing a surface-reformed zinc oxide water-based suspension in which the content rate of surface-reformed zinc oxide was 10% by mass.

Next, the same mass of an aqueous solution of calcium chloride (25% by mass of calcium chloride dihydrate) as the mass of the surface-reformed zinc oxide in the suspension was added thereto and stirred, and the suspension was left to stand for two hours.

Next, this suspension was separated into solid and liquid using a centrifugal separator three times, and the obtained solid substance was dried at 150° C., thereby producing zinc oxide which is coated with silicon oxide of Example 5.

Meanwhile, when solid-liquid separation was repeated, solid-liquid separation was carried out using a centrifugal separator under the same conditions, that is, the same concentration and the same mass of an aqueous solution as those of the aqueous solution of calcium chloride which had been initially used was added to the solid substance obtained by means of the solid-liquid separation was added thereto.

Example 6

A commercially available product SIH20-ZnO650 (the average particle diameter of 25 nm, $SiO_2/ZnO=17\%$ by mass; manufactured by Sumitomo Osaka Cement Co., Ltd.) was used as surface-reformed zinc oxide, this surface-reformed zinc oxide and water were mixed together, and then, ultrasonic dispersion was carried out, thereby preparing a surface-reformed zinc oxide water-based suspension in which the content rate of surface-reformed zinc oxide was 10% by mass.

Next, the same mass of an aqueous solution of calcium chloride (25% by mass of calcium chloride dihydrate) as the mass of the surface-reformed zinc oxide in the suspension was added thereto and stirred, and the suspension was left to stand for two hours.

Next, this suspension was separated into solid and liquid using a centrifugal separator three times, and the obtained solid substance was dried at 150° C., thereby producing zinc oxide which is coated with silicon oxide of Example 6.

Meanwhile, when solid-liquid separation was repeated, solid-liquid separation was carried out using a centrifugal separator under the same conditions, that is, the same concentration and the same mass of an aqueous solution as those of the aqueous solution of calcium chloride which had been initially used was added to the solid substance obtained by means of the solid-liquid separation was added thereto.

Example 7

A suspension including silicate soda was produced according to Example 1.

Next, this suspension was heated to 60° C., and a diluted acid was gradually added to the suspension under stirring so as to adjust the pH to be 6.5 to 7. After that, the suspension was left to stand for two hours, then, furthermore, the same mass of an aqueous solution of magnesium chloride (25% by mass of magnesium chloride hexahydrate) as the mass of the zinc oxide particles in the suspension was added thereto and stirred, and the suspension was left to stand for additional two hours.

Next, this suspension was separated into solid and liquid using a centrifugal separator, and the obtained solid substance was cleaned with water. After that, the solid substance was dried at 150° C., and furthermore, a thermal treatment (calcination) was carried out at 500° C. for two hours, thereby producing zinc oxide which is coated with silicon oxide of Example 7.

Example 8

Zinc oxide particles (the average particle diameter of 250 nm; manufactured by Sumitomo Osaka Cement Co., Ltd.) and water were mixed together, and then, ultrasonic dispersion was carried out, thereby preparing a zinc oxide water-based suspension in which the content rate of zinc oxide was 50% by mass.

Next, this zinc oxide water-based suspension was added to an aqueous solution of silicate soda including 20% by mass of silicate soda of the mass of the zinc oxide particles in the zinc oxide water-based suspension in terms of silicon oxide and was strongly stirred, thereby producing a suspension.

Next, this suspension was heated to 60° C., a diluted acid was gradually added to the suspension under stirring so as to adjust the pH to be 6. After that, the suspension was left to stand for two hours, then, furthermore, the same mass of an aqueous solution of calcium chloride (25% by mass of calcium chloride dihydrate) as the mass of the zinc oxide particles in the suspension was added thereto and stirred, and the suspension was left to stand for additional two hours.

Next, this suspension was separated into solid and liquid using a centrifugal separator, and the obtained solid substance was cleaned with water. After that, the solid substance was dried at 150° C., and furthermore, a thermal treatment (calcination) was carried out at 500° C. for two hours, thereby producing zinc oxide which is coated with silicon oxide of Example 8.

Comparative Example 1

Zinc oxide particles (the average particle diameter of 35 nm; manufactured by Sumitomo Osaka Cement Co., Ltd.) and water were mixed together, and then, ultrasonic dispersion was carried out, thereby preparing a zinc oxide water-based suspension in which the content rate of zinc oxide was 20% by mass.

Next, this zinc oxide water-based suspension was added to an aqueous solution of silicate soda including 20% by mass of silicate soda of the mass of the zinc oxide particles in the zinc oxide water-based suspension in terms of silicon oxide and was strongly stirred, thereby producing a suspension.

Next, this suspension was heated to 60° C., a diluted acid was gradually added to the suspension under stirring so as to adjust the pH to be 6.5 to 7. After that, the suspension was left to stand for two hours, this suspension was separated into solid and liquid using a centrifugal separator, and the obtained solid substance was cleaned with water. After that, the solid substance was dried at 150° C., and furthermore, a thermal treatment (calcination) was carried out at 500° C. for two hours, thereby producing zinc oxide which is coated with silicon oxide of Comparative Example 1.

Comparative Example 2

Zinc oxide which is coated with silicon oxide was produced according to Comparative Example 1.

Next, this zinc oxide which is coated with silicon oxide and 2-propanol were mixed together, and then, ultrasonic dispersion was carried out, thereby preparing a zinc oxide which is coated with silicon oxide 2-propanol suspension in which the content rate of zinc oxide which is coated with silicon oxide was 10% by mass.

Next, this suspension was heated to 60° C., ammonia water and water were added to the suspension under stirring so as to adjust the pH to be 10 to 11. Meanwhile, the amount of water added was set to be 120% by mass of tetramethoxysilane in a tetramethoxysilane 2-propanol solution that was added afterwards.

Furthermore, the tetramethoxysilane 2-propanol solution was slowly added dropwise to this suspension so that the amount of tetramethoxysilane added dropwise reached 15% by mass of the total mass of the zinc oxide in terms of silicon oxide and was continuously stirred for six hours.

After the end of the reaction, this suspension was separated into solid and liquid using a centrifugal separator, and the obtained solid substance was dried at 120° C. Next, a thermal treatment (calcination) was carried out on this dried substance at 500° C. for two hours, thereby producing zinc oxide which is coated with silicon oxide of Comparative Example 2.

Comparative Example 3

Zinc oxide particles (the average particle diameter of 35 nm; manufactured by Sumitomo Osaka Cement Co., Ltd.) and water were mixed together, and then, ultrasonic dispersion was carried out, thereby preparing a zinc oxide water-based suspension in which the concentration of zinc oxide was 50 g/L (5% by mass).

Next, this suspension was heated to 80° C., and an aqueous solution of sodium silicate was added to this suspension under stirring so as to be 10% by mass of zinc oxide in terms of silicon oxide, and the mixture was aged for 10 minutes.

Next, a diluted acid was added to the suspension under stirring over 60 minutes so as to adjust the pH to be 6.5, and the mixture was aged for 30 minutes.

Next, an aqueous solution of sodium aluminate was added to this suspension under stirring so as to be 5% by mass of the total mass of zinc oxide in terms of aluminum oxide, and the mixture was aged for 10 minutes.

Next, a diluted acid was added to the suspension under stirring over 10 minutes so as to adjust the pH to be 7.0, and the mixture was aged for 30 minutes.

Next, this suspension was separated into solid and liquid using a centrifugal separator, was cleaned with water, and the obtained solid substance was heated and dried at 130° C. for five hours. Next, the dried substance was crushed using a jet mill, thereby producing zinc oxide which is coated with silicon oxide of Comparative Example 3.

Comparative Example 4

An aqueous solution of sodium silicate was added to zinc oxide particles (the average particle diameter of 35 nm; manufactured by Sumitomo Osaka Cement Co., Ltd.) so as to be 9% by mass of the zinc oxide particles in terms of silicon oxide, was strongly stirred so as to produce a suspension, a diluted acid was gradually added to this suspension under stirring so as to adjust the pH to be 7, and the mixture was left to stand for four hours. Then, an oxide of silicon was gradually precipitated on the surfaces of zinc oxide particles, and coatings were formed on the surfaces.

Next, this suspension was separated into solid and liquid using a centrifugal separator, was cleaned with water, and the obtained solid substance was heated and dried at 105° C. for 24 hours, thereby producing zinc oxide which is coated with silicon oxide of Comparative Example 4.

[Evaluation]

The respective zinc oxide which is coated with silicon oxides of Examples 1 to 8 and Comparative Examples 1 to 4 were evaluated. The evaluation items are as described below. In addition, the commercially available product SIH20-ZnO650 which was used in Example 6 was evaluated as Comparative Example 5.

(1) Evaluation of pH

The zinc oxide which is coated with silicon oxide (2 g) was injected into ion-exchange water (98 g), was stirred for 20 hours so as to produce a zinc oxide which is coated with silicon oxide-containing water dispersion liquid, and the pH of a supernatant liquid obtained by means of the solid-liquid separation of this dispersion liquid using a centrifugal separator. The pH of the supernatant liquid is preferably near 7.

(2) Contents of Na, Ca, and Mg

The contents of Na, Ca, and Mg in the zinc oxide which is coated with silicon oxide were measured by means of atomic absorption spectrometry.

(3) Degree of Condensation of Silicon Oxide

The NMR spectrums of the zinc oxides coated with silicon oxide were measured by means of MAS-nuclear magnetic resonance (NMR) spectroscopy in which solid $^{29}Si$ was used, and the area ratios $Q^0$, $Q^1$, $Q^2$, $Q^3$, and $Q^4$ of signals belonging to individual environments $Q^0$, $Q^1$, $Q^2$, $Q^3$, and $Q^4$ were calculated from the peak area ratios of these NMR spectra.

The values of $Q^3+Q^4$ and the values of $Q^4/(Q^3+Q^4)$ were calculated in which the abundance ratio of silicon in the silicon oxide coatings in the $Q^3$ environment was denoted by $Q^3$, and the abundance ratio in the silicon oxide coatings in the $Q^4$ environment was denoted by $Q^4$, and cases in which $Q^3+Q^4 \geq 0.6$ was satisfied were marked using "O", and cases in which $Q^3+Q^4 \geq 0.6$ was not satisfied were marked using "X". In addition, cases in which $Q^4/(Q^3+Q^4) \geq 0.5$ was satisfied were marked using "O", cases in which $Q^4/(Q^3+Q^4) \geq 0.5$ was not satisfied were marked using "X".

(4) Decomposition Rate of Brilliant Blue

An aqueous solution of Brilliant Blue in which the content rate of Brilliant Blue was adjusted to be 5 ppm was produced, 0.15 g of zinc oxide which is coated with silicon oxide in terms of zinc oxide was injected into the aqueous solution of Brilliant Blue (15 g), a suspension was adjusted by means of ultrasonic dispersion, the suspension was irradiated using an ultraviolet lamp (the central wavelength: 254 nm) from an irradiation distance of 10 cm for six hours, and then a supernatant liquid was sampled.

Next, the absorptiometric spectrum of each of the aqueous solution of Brilliant Blue and the supernatant liquid were measured by means of atomic absorption spectrometry, and the decomposition rate D of Brilliant Blue was calculated from Equation (1) above using the measured values.

These evaluation results are shown in Table 1.

calcium, the content of sodium decreased, the content of calcium increased, and the pH changed to the alkali side to a small extent.

Similarly, it was confirmed that, when calcium or magnesium and sodium were substituted, it was possible to suppress the change of pH to the alkali side by comparing Examples 2 and 3 and Comparative Example 2, Example 4 and Comparative Example 3, Example 5 and Comparative Example 4, and Example 6 and Comparative Example 5, respectively.

In addition, it was confirmed that, in the zinc oxide which is coated with silicon oxides of Examples 2 and 3, compared with the zinc oxide which is coated with silicon oxides of Examples 1 and 4 to 8, the $Q^3+Q^4$ value and the $Q^4/(Q^3+Q^4)$ value which exhibited the degree of condensation of silicon oxide were higher, and the zinc elution rates were lower.

INDUSTRIAL APPLICABILITY

The zinc oxide which is coated with silicon oxide of the present invention contains at least one element selected from a group consisting of Mg, Ca, and Ba, and thus, even in a case in which the zinc oxide which is coated with silicon oxide is applied to water-based materials such as water-based cosmetics, it is possible to suppress a change in the hydrogen-ion exponents (pH) of the water-based materials.

TABLE 1

| | | Metal ion (% by mass) | | | Degree of condensation of silicon oxide | | Decomposition rate of Brilliant |
|---|---|---|---|---|---|---|---|
| | pH | Na | Ca | Mg | $Q^2 + Q^4 \geq 0.6$ | $Q^4/(Q^2 + Q^4) \geq 0.5$ | Blue (%) |
| Example 1 | 9.1 | 0.53 | 0.92 | N.D. | O | X | — |
| Example 2 | 9.2 | 0.27 | 0.69 | N.D. | O | O | <1.0 |
| Example 3 | 8.2 | 0.12 | 0.44 | N.D. | O | O | <1.0 |
| Example 4 | 8.1 | 0.01 | 0.02 | N.D. | X | X | — |
| Example 5 | 7.1 | 0.06 | 0.79 | N.D. | X | X | — |
| Example 6 | 7.9 | 0.09 | 0.81 | N.D. | X | X | — |
| Example 7 | 9.2 | 0.54 | N.D. | 0.55 | O | X | — |
| Example 8 | 7.8 | 0.09 | 0.13 | N.D. | O | X | — |
| Comparative Example 1 | 9.7 | 1.00 | N.D. | N.D. | O | X | — |
| Comparative Example 2 | 9.7 | 0.87 | N.D. | N.D. | O | O | <1.0 |
| Comparative Example 3 | 8.8 | 0.12 | N.D. | N.D. | X | X | — |
| Comparative Example 4 | 10.3 | 0.38 | N.D. | N.D. | X | X | — |
| Comparative Example 5 | 9.3 | 0.57 | N.D. | N.D. | X | X | — |

(Note)
N.D. = not detected

According to Table 1, in the zinc oxide which is coated with silicon oxides of Examples 1 to 8, it was found that, compared with the zinc oxide which is coated with silicon oxide of Comparative Examples 1 to 4, the contents of any one of Ca and Mg were higher, and the contents of Na were lower, and thus a smaller amount of Na eluted. Therefore, it was found that the pH of the supernatant liquid changed to the alkali side to a smaller extent.

Specifically, the difference between Example 1 and Comparative Example 1 was whether or not the substitution step was performed for calcium and sodium, and therefore the pH of Example 1 in which the substitution step was carried out was nearer to 7 than the pH of Comparative Example 1 in which the substitution step was not carried out. That is, it was confirmed that, since sodium was substituted with Therefore, the zinc oxide which is coated with silicon oxide of the present invention is capable of maintaining the stability of the qualities of the water-based materials and is thus capable of improving the degree of freedom in terms of formulation in a case in which the zinc oxide is applied to water-based cosmetics in which it is necessary to suppress a change in the hydrogen-ion exponents (pH) of the water-based materials.

The invention claimed is:

1. Zinc oxide which is coated with silicon oxide, wherein the surfaces of zinc oxide particles are coated with silicon oxide coatings, and the coated zinc oxide particles comprise at least one element selected from the group consisting of Mg, Ca, and Ba;
wherein, when an abundance ratio of silicon included in the silicon oxide coatings in a $Q^3$ environment is denoted by $Q^3$, and the abundance ratio of silicon included in the silicon oxide coatings in a $Q^4$ environment is denoted by $Q^4$, the abundance ratios satisfy $Q^3+Q^4 \geq 0.6$ and $Q^4/(Q^3+Q^4) \geq 0.5$, and a decomposition rate of Brilliant Blue generated by a photocatalytic activity of the coated zinc oxide particles is 3% or less.

2. The zinc oxide which is coated with silicon oxide according to claim 1, wherein the silicon oxide coatings include said at least one element selected from a group consisting of Mg, Ca, and Ba, further comprises an alkali metal, and a total mass percentage of the element included in the silicon oxide coating is greater than a mass percentage of an alkali metal included in the silicon oxide coatings.

3. The zinc oxide which is coated with silicon oxide according to claim 2, wherein the sum total of the mass percentages of the alkali metals is 0.8% by mass or less.

4. A composition which includes zinc oxide coated with silicon oxide, wherein the composition comprises the zinc oxide which is coated with silicon-oxide according to claim 1.

5. A cosmetic comprising:
the zinc oxide which is coated with silicon oxide according to claim 1 in a cosmetic base material thereof.

6. The zinc oxide which is coated with silicon oxide according to claim 1,
wherein the silicon oxide coatings include said at least one element selected from a group consisting of Mg, Ca, and Ba, and a total mass percentage of the element included in the silicon oxide coating is 0.01% to 1% by mass.

7. The zinc oxide which is coated with silicon oxide according to claim 1,
wherein the average particle diameter of the zinc oxide is 2 nm to 500 nm.

8. The zinc oxide which is coated with silicon-oxide according to claim 2,
wherein the ratio of the mass percentage of the alkali metal included in the silicon oxide coatings to the total mass percentage of said at least one element selected from the group consisting of Mg, Ca, and Ba included in the silicon oxide coatings is 0.001 to 0.6.

* * * * *